United States Patent
Blackburn et al.

(10) Patent No.: US 10,197,521 B2
(45) Date of Patent: *Feb. 5, 2019

(54) ELECTRIC-FIELD ENHANCED PERFORMANCE IN CATALYSIS AND SOLID-STATE DEVICES INVOLVING GASES

(71) Applicant: University of Florida Research Foundation, Incorporated, Gainesville, FL (US)

(72) Inventors: Bryan M. Blackburn, Silver Spring, MD (US); Eric D. Wachsman, Fulton, MD (US); Frederick Martin Van Assche, IV, Maitland, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 480 days.

This patent is subject to a terminal disclaimer.

(21) Appl. No.: 14/714,860

(22) Filed: May 18, 2015

(65) Prior Publication Data

US 2015/0253275 A1    Sep. 10, 2015

Related U.S. Application Data

(63) Continuation of application No. 12/743,490, filed as application No. PCT/US2008/086693 on Dec. 12, 2008, now Pat. No. 9,034,170.

(Continued)

(51) Int. Cl.
*G01N 27/30* (2006.01)
*G01N 27/407* (2006.01)
(Continued)

(52) U.S. Cl.
CPC ........... *G01N 27/30* (2013.01); *G01N 27/406* (2013.01); *G01N 27/4074* (2013.01);
(Continued)

(58) Field of Classification Search
None
See application file for complete search history.

(56) References Cited

U.S. PATENT DOCUMENTS 3,149,921 A * 9/1964 Warner ................ G01N 27/404
                                                    205/782.5
3,475,882 A   11/1969 Hoenig
(Continued)

FOREIGN PATENT DOCUMENTS

EP    0 851 226 A2    7/1998
JP    09-113482       5/1997
(Continued)

OTHER PUBLICATIONS

Blackburn et al. Multifunctional Potentiometric Gas Sensor Array with an Integrated Heater and Temperature Sensors, in Advances in Electronic Ceramics: Ceramic Engineering and Science Proceedings, vol. 28, Issue 8, eds. C. Randall, H.-T. Lin, K. Koumoto, P. Clem, J. Salem and D. Zhu, John Wiley & Sons, Inc., Hoboken, NJ, USA, published Oct. 2007.*

(Continued)

*Primary Examiner* — Gurpreet Kaur
*Assistant Examiner* — Steven E Rosenwald
(74) *Attorney, Agent, or Firm* — Saliwanchik, Lloyd & Eisenschenk

(57) ABSTRACT

Electrode configurations for electric-field enhanced performance in catalysis and solid-state devices involving gases are provided. According to an embodiment, electric-field electrodes can be incorporated in devices such as gas sensors and fuel cells to shape an electric field provided with respect to sensing electrodes for the gas sensors and surfaces of the fuel cells. The shaped electric fields can alter surface dynamics, system thermodynamics, reaction kinetics, and adsorption/desorption processes. In one embodiment, ring-shaped electric-field electrodes can be provided around sensing electrodes of a planar gas sensor.

17 Claims, 28 Drawing Sheets

Related U.S. Application Data

(60) Provisional application No. 61/013,287, filed on Dec. 12, 2007.

(51) Int. Cl.
  *H01M 8/0432* (2016.01)
  *H01M 8/04537* (2016.01)
  *G01N 27/406* (2006.01)

(52) U.S. Cl.
  CPC ...... *G01N 27/4075* (2013.01); *H01M 8/0432* (2013.01); *H01M 8/04537* (2013.01); *H01M 8/04574* (2013.01); *Y02E 60/50* (2013.01)

(56) References Cited

U.S. PATENT DOCUMENTS

| | | | |
|---|---|---|---|
| 4,795,968 A | 1/1989 | Madou et al. | |
| 5,389,218 A | 2/1995 | Bonne et al. | |
| 5,389,225 A | 2/1995 | Aagard et al. | |
| 5,841,021 A * | 11/1998 | De Castro | G01N 27/4162 204/424 |
| 6,916,415 B2 | 7/2005 | Walde | |
| 7,264,700 B1 | 9/2007 | Garzon et al. | |
| 7,294,252 B2 | 11/2007 | Wang et al. | |
| 2002/0148278 A1* | 10/2002 | Eastman | G01N 27/18 73/25.03 |
| 2004/0026268 A1 | 2/2004 | Maki et al. | |
| 2004/0229095 A1* | 11/2004 | Pearson | H01M 8/04679 429/431 |
| 2005/0034987 A1 | 2/2005 | Zhou et al. | |
| 2005/0069892 A1 | 3/2005 | Iyengar et al. | |
| 2005/0235735 A1 | 10/2005 | Doll et al. | |
| 2006/0076338 A1 | 4/2006 | Kagan | |
| 2006/0189142 A1 | 8/2006 | Saito et al. | |
| 2007/0080075 A1 | 4/2007 | Wang et al. | |
| 2008/0110241 A1 | 5/2008 | Rothschild et al. | |

FOREIGN PATENT DOCUMENTS

| | | | |
|---|---|---|---|
| JP | 2000-180400 A | 6/2000 | |
| JP | 2003-187822 A * | 4/2003 | ............. H01M 8/02 |
| JP | 2003-187822 A | 7/2003 | |
| JP | 2006-133039 A | 5/2006 | |
| KR | 20030055341 A1 | 7/2003 | |
| WO | WO 02/46734 A1 | 6/2002 | |
| WO | WO 03/076921 A2 | 9/2003 | |
| WO | WO 2005/036158 A1 | 4/2005 | |

OTHER PUBLICATIONS

Chiou et al. Electroanalysis, 8, 1996, 1179-1182.*
Blackburn, B.M., et al., "Electric-Field Effects in Solid-State Ionic Devices," *ECS Transactions*, 2009, 16(51):355-166.
Blackburn, Bryan M. et al., "Multifunctional Potentiometric Gas Sensory Array With an Integrated Heater and Temperature Sensors," *Advances in Electronic Ceramics: Ceramic Engineering and Science Proceedings*, 2008, The American Ceramic Society, 28(8):101-108.
Blueh, O. "Gas Adsorption in an Electrical Field," *Zeitzchift fur Physik*, 1937, 107(5-6):369-381, translated by Translation Consultants, Ltd., Arlington, VA, for the National Aeronautics and Space Administration, Aug. 1971.
Hellmich, W., et al., "Field-Effect-Induced Gas Sensitivity Changes in Metal Oxides," *Sensors and Actuators B*, 1997, 43:132-139.
Mallinson, Richard G., et al., "Enhancement of Methane Conversion Using Electric Fields," *Quarterly Report for U.S. Department of Energy*, DOE/MC/31170, Nov. 1995.
Minh, Nguyen Q. "Ceramic Fuel Cells," *J. Am. Ceram. Soc.*, 1993, 76(3):563-588.
Röder-Roith, U., et al., "Thick-Film Solid Electrolyte Oxygen Sensors Using the Direct Ionic Thermoelectric Effect," *Sensors and Actuators B*, 2009, 136:530-535.
Storm, U., et al. "A Resistive Gas Sensor with Elimination and Utilization of Parasitic Electric Fields," *Sensors and Actuators B*, Jun. 2001, 77(1-2):529-533.
Woo, Leta Y., et al., "Impedance Characterization of a Model Au/Yttria-Stabilized Zirconia/Au Electrochemical Cell in Varying Oxygen and $No_x$ Concentrations," *Journal of the Electrochemical Society*, 2007, 154(4):J129-J135.
Yu, Ji Haeng et al., "Non-Ohmic Current-Voltage and Impedance Characteristics of Electroadsorptive $Zn_2SnO_4$," *Journal of the Electrochemical Society*, 2001, 148(6):G307-G314.
Wachsman, E.D. et al., "Electrocatalytic reduction of $NO_x$ on $La_{1-x}A_xB_{1-y}B^1{}_yO_{3-\sigma}$: evidence of electrically enhanced activity," *Solid State Ionics*, 2000, vol. 136-137, pp. 775-782.
Yoo, J. et al., "Influence of Adsorption and Catalytic Reaction on Sensing Properties of a Potentiometric $La_2CuO_4$/YSZ/PT Sensor," *Journal of the Electrochemical Society*, 2007, vol. 154, pp. J190-J195.

* cited by examiner

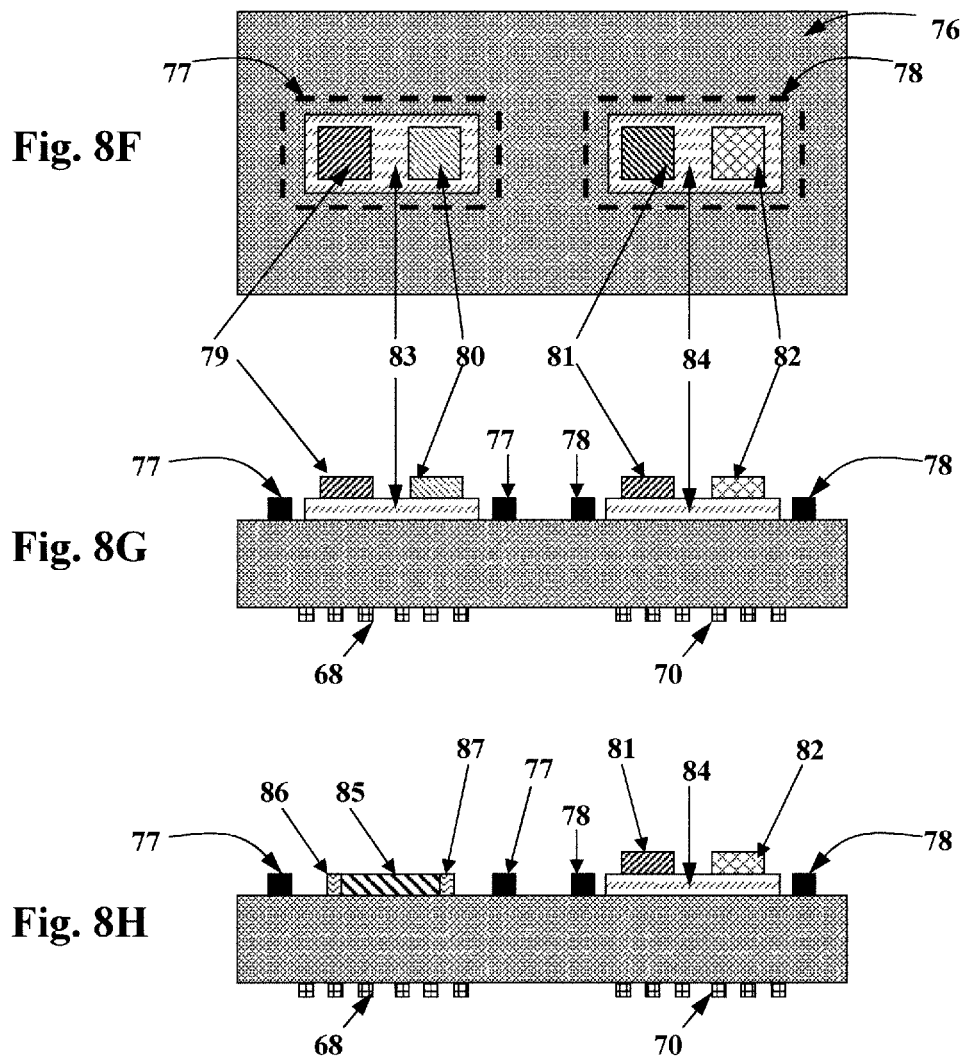

ELECTRIC-FIELD ENHANCED PERFORMANCE IN CATALYSIS AND SOLID-STATE DEVICES INVOLVING GASES

CROSS-REFERENCE TO RELATED APPLICATION

The present application is a continuation of U.S. application Ser. No. 12/743,490, filed Aug. 23, 2010, which is the U.S. National Stage application of International Patent Application No. PCT/US2008/086693, filed on Dec. 12, 2008, which claims the benefit of U.S. Provisional Application Ser. No. 61/013,287, filed Dec. 12, 2007, all of which are hereby incorporated by reference herein in their entirety, including any figures, tables, or drawings.

The subject invention was made with government support under a research project supported by the Department of Energy, Contract No. DE-FC26-03NT41614. The government has certain rights to this invention.

BACKGROUND OF INVENTION

An electrochemical cell is the coupling of two electrode materials between an ionic conductor, whereby electrochemical reactions occur at the interface between the ionic conductor, an electrode, and gas. The electrode materials are typically metal or semiconductor and the ionic conductor is typically an electrolyte. Electrodes may also include mixed electronic/ionic materials. Currently, yttria stabilized zirconia (YSZ) is being used as the electrolyte material for certain gas sensors and fuel cells.

Electrochemical cells may operate in open-circuit mode or may be used to drive reactions with the application of current or voltage to the cell. Electrochemical cells are used in many devices, such as gas sensors and fuel cells, and applications, such as electroplating. Electrochemical cells are also used in catalysis for the conversion of reactants into useful byproducts.

A gas sensor is a device that detects the concentration or presence of a single or multiple gas species. A gas sensor may, but need not, include an electrochemical cell. A gas sensor without an electrochemical cell can be considered a non-electrochemical device. A gas sensor may have different transduction mechanisms for detecting gas and may be multifunctional by detecting multiple gas species. For example, potentiometric, amperometric, or impedancemetric transduction mechanisms may be used. One issue with most gas sensors is cross-interference from other species, or poor selectivity.

A fuel cell is a device that directly converts chemical energy into electrical energy for power consumption in applications such as for automobiles and homes. A solid oxide fuel cell (SOFC) is one type of fuel cell that incorporates a solid electrolyte sandwiched between at least two electrodes, one electrode functioning as a cathode and the other electrode functioning as an anode. Fuel cells may also be incorporated into stacks in order to increase power output. In the case where the electrolyte is an oxygen ion conductor, oxygen reacts at the cathode and is transported to the anode through the electrolyte as an ion where the oxygen electrochemically reacts with fuel, such as, for example, $H_2$ or CO, to produce electricity.

In certain devices using electrochemical cells, Non-Faradaic Electrochemical Modification of Catalytic Activity (NEMCA) is incorporated for the enhancement of catalytic reactions through the direct application of voltage or current to the electrodes in an electrochemical cell.

In catalysis, the kinetics of a reaction involves the process of changing rates of intermediate steps and other processes during a reaction. These changes affect the overall reaction rate.

The energetics of a reaction refers to the many different energy barriers to activating the steps of a reaction. As an example, a diffusion barrier is one type of energy barrier. These barriers can be overcome by adding energy to the system. Often thermal energy is used to overcome the barriers.

A reaction pathway is the steps that a reaction follows as it proceeds from starting reactants to final products. The pathway that a reaction follows has to do, in part, with the kinetics and energetics of the system. Adsorption and desorption are processes where gas molecules from the gas phase are trapped (physisorption) or bonded to the surface (chemisorption). These processes often also affect the kinetics and energetics of a reaction.

Surface relaxation involves the motion of entire adlayer(s), while surface reconstruction involves changes in the surface periodicity. Both processes can change the way a reaction proceeds. Surface dynamics may refer to the processes that involve dynamic motion on a surface, such as gas (phase) molecules colliding with a surface or diffusion of a species on a surface.

A catalyst may exist as part of an electrochemical device or atop a "catalyst support" which acts to either provide a certain structure for the catalysts or to disperse the catalyst among different reaction sites.

One major problem in catalysis is diminished conversion due to the presence of "poisons." The presence of "poisons" can also have negative impacts in gas sensors, fuel cells, and other related devices. Poisons may block adsorption sites or cause phase reconstruction; the latter case may be caused by poisons forming complexes with, for instance, oxygen species from an electrolyte, and possibly followed by desorption of the complex. This may prevent certain mechanisms from occurring that rely on the presence of that oxygen, thereby inhibiting the device or catalyst from performing properly.

BRIEF SUMMARY

Embodiments of the present invention relate to electric field enhancement of chemical and/or electrochemical reactions. An electric field can be produced and shaped to alter gas adsorption and other chemical reactions for various applications. The generated electric field can be provided using electric-field electrodes, which are conductive surfaces purposefully biased so as to generate an electric field. Certain embodiments of the present invention can be applied to gas sensors, fuel cells, and other electrochemical devices. In addition, certain embodiments can be used to improve the performance of electrochemically promoted reactions (NEMCA) and any other general catalysis reaction involving at least one gaseous species, such as, for example, ethylene oxidation. Electric-field electrodes arranged according to an embodiment of the present invention can also be applied to non-electrochemical devices such as gas sensors that do not utilize an electrolyte.

In an embodiment, electric-field electrodes can be applied to a gas sensor. The electric-field electrodes can be arranged to improve sensitivity, selectivity, and response time in the gas sensor.

In one embodiment, the electric-field electrodes can be positioned to apply an electric field parallel to a sensing electrode of the gas sensor.

In another embodiment, electric-field electrodes can be applied to a gas sensor for shaping the electric field profile. In such an embodiment, electric-field electrodes can be positioned with respect to the sensing electrodes of the gas sensor to apply a desired electric field profile with respect to specific locations on a device or catalyst support. The electric fields can be shaped to be perpendicular, parallel, or any angle in between with respect to a particular local reaction zone or entire device. In addition, the relative strengths of the electric fields at different regions of the device can be different. In a further embodiment, the electric-field electrodes can be applied to a gas sensor incorporating an air-reference electrode.

In an embodiment, electric-field electrodes can be applied to a fuel cell. The electric-field electrodes can be used to stabilize/destabilize adsorbate complexes on a surface and remove or inhibit buildup of poisons from a fuel cell surface.

Electric-field electrodes arranged according to an embodiment of the present invention can be applied for altering the localized fields that exist around a dipole layer region in an electrochemical system using the externally generated electric fields.

"Electric-field electrodes" may be used to enhance chemical/electrochemical reactions and performance in various devices and applications. Such "Electric-field electrodes" may be effectively and actively shaped to achieve enhanced performance. In embodiments for electrochemical devices, little or no (ionic or electronic) current or charge is introduced to the metal/electrolyte or semiconductor/electrolyte interface. Furthermore, the such "Electric-field electrodes" may incorporate any other structure or component of the device that has at least one additional purpose other than to contribute to the shape of the electric field.

Voltage may be applied with a battery or other voltage source where more than one voltage source may be used if desired. One or more voltage signals may be distributed with a microcontroller, multiplexer, (resistive) voltage divider, and/or other means of applying different voltage magnitudes or bias schemes to various "electric-field electrodes".

There are numerous techniques that can be employed in the manufacture of these devices. Multiple devices may be made simultaneously and separated by various means after manufacture. Furthermore, these and other techniques may be used to deposit catalysts on electric-field enhanced catalyst supports. Any combination of the following techniques or other techniques known to those skilled in the art may be used:

i) Multilayer Fabrication
tape-casting, screen-printing;
ii) Bottom-Up (Additive) Approach
direct-write methods (e.g., pump- or aerosol-based deposition), dip coating, spin coating, laser sintering;
iii) Multi-Step (Subtractive) Approach
microfabrication using photolithography and other techniques used in the fabrication of microelectronics and micro-electro-mechanical systems (MEMS), electron-beam and laser-based subtractive fabrication, laser micromachining;
iv) Wire Attachment Methods and Metallization
metals used for metallization or wire attachment are preferably able to withstand harsh environments, wire bonding (e.g., Au or Pt wire), brazing, and/or any other method of wire attachment. Different metallization may exist in multiple layers and connected to each other by vias that exist in between layers;

v) Device Packaging
standard or new packaging techniques and designs of high-temperature (or any other) electronics and/or sensors may be used with this device; and
vi) Catalyst Deposition
catalyst materials may be deposited onto supports using any method such as spin coating, dip coating, or thermal spraying.

Embodiments of the subject invention can be directed to performance enhanced gas sensors, fuel cells, and other electrochemical or non-electrochemical devices, enhanced catalytic reactions in chemical processing and improved catalytic converters. Embodiments can achieve lower costs, increased productivity, efficiency and/or accuracy depending on the application, including automobile manufacturers, sensor companies, electric utility companies, and/or chemical manufacturing companies.

BRIEF DESCRIPTION OF DRAWINGS

FIG. 1A shows a cross-sectional view of the planar gas sensor with electric field applied parallel to the sensing electrodes according to an embodiment of the present invention, FIG. 1B shows a top view of the planar gas sensor of FIG. 1A, and FIG. 1C shows a bottom view of the planar gas sensor of FIG. 1A.

FIG. 2A shows a cross-sectional view of the planar gas sensor with electric-field electrodes for actively shaping the electric field according to an embodiment of the present invention, FIG. 2B shows a top view of the planar gas sensor of FIG. 2A, and FIG. 2C shows a bottom view of the planar gas sensor of FIG. 2A.

FIG. 5A shows a cross-sectional view of the planar gas sensor with air-reference electrode according to an embodiment of the present invention, FIG. 5B shows a top view of the planar gas sensor of FIG. 5A, and FIG. 5C shows a bottom view of the planar gas sensor of FIG. 5A.

FIG. 6C shows a sensitivity plot and $NO_x$ levels for a sensor exposed to NO, and FIG. 6D shows a sensitivity plot and NOx levels for a sensor exposed to $NO_2$.

FIGS. 7B and 7C show desorption profiles for measured NO and $NO_2$, respectively, with initial adsorption of NO at 300° C. according to an embodiment of the present invention, and FIGS. 7D and 7E show desorption profiles for measured NO and $NO_2$, respectively, with initial adsorption of $NO_2$ at 300° C. according to an embodiment of the present invention.

FIGS. 8A-8F show various other possible configurations for devices (including gas sensors) utilizing the electric-field enhancements. FIG. 8A shows a top view of a substrate (electrolyte or other material), with each sensing electrode surrounded with a number of "electric-field electrodes" forming a dashed ring shape around the sensing electrodes. FIG. 8B shows the cross-section of 8A, with the sensing electrodes and "electric-field electrodes" displayed on one surface and heater structures (serpentine or other pattern) on a second surface. FIG. 8C shows the cross-section of 8A, but now with the "electric field electrodes" and heater structures embedded within the substrate, and a new layer (electrolyte or other material) between the substrate and sensing electrodes.

FIGS. 8D and 8E show cross-sections of 8A, with heater structures embedded in the substrate and second layer between substrate and sensing electrodes; the electric-field electrodes now form plate-like shapes rather than a dashed arrangement. Furthermore, 8D shows structure that creates a cavity above each sensing electrode; the electric field electrodes are attached to the inner side of this structure. FIG. 8E shows a similar cavity-creating structure, but with the electric field electrodes on the top of this structure.

FIGS. 8F-8H show several additional configurations of devices utilizing the electric-field enhancements. 8F shows the top view of the embodiment with two rectangular layers on top of the substrate containing at least two sensing electrodes each. Several electric field electrodes surround each of these rectangular layers in a dashed arrangement. 8G shows a cross-section of 8F, with rectangular layers and corresponding sensing electrodes and electric-field electrodes. Heating structures are shown on the bottom surface. FIG. 8H shows another possible embodiment where one of the rectangular regions with sensing electrodes on top is replaced with a gas sensitive material in contact with the substrate. Electrical contacts are made to this material in two places. The remainder of this embodiment is the same as in 8G.

FIG. 9A shows a cross-sectional view of the electrochemical device (e.g., a fuel cell) with electric-field electrodes according to an embodiment of the present invention, FIG. 9B shows a top view of the electrochemical device (e.g., a fuel cell) of FIG. 9A, and FIG. 9C shows a bottom view of the electrochemical device (e.g., a fuel cell) of FIG. 9A.

FIG. 10A shows a cross-sectional view of the electrochemical device (e.g., a fuel cell) with electric-field electrodes in a planar configuration according to an embodiment of the present invention, FIG. 10B shows a top view of the electrochemical device (e.g., a fuel cell) of FIG. 10A, and FIG. 10C shows a bottom view of the electrochemical device (e.g., a fuel cell) of FIG. 10A.

FIG. 11A shows a cross-sectional view of the catalyst bed used for catalysis processes according to an embodiment of the present invention, FIG. 10B shows a top view of the polygonal-cylinder shape of the catalyst bed of FIG. 11A, and FIG. 11C shows a representation of catalyst particles.

DETAILED DISCLOSURE

Figure 1A:
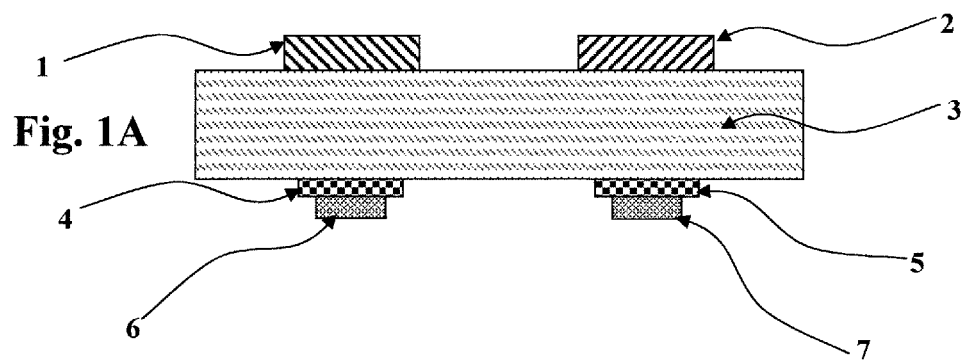
FIGS. 1A-1C show a planar gas sensor according to an embodiment of the present invention.

Embodiments of the present invention pertain to enhancement of chemical reactions and associated processes through the use of specifically created (or "shaped") electric fields around the device or location of the reaction or process. The shaped electric fields can be used to improve performance in several applications, including the use in gas sensors, fuel cells, and other electrochemical devices, such as, for example, hydrogen separation membranes. The shaped electric fields can also be used to improve the performance of electrochemically "promoted" reactions such as non-faradaic electrochemical modification of catalytic activity (NEMCA), which are known to enhance catalytic rates through the direct bias of an electrochemical cell. In addition, the "shaped" electric field can be used to enhance any general catalysis reaction involving gaseous species. For example, gas reforming and general catalytic conversion can be enhanced. This includes enhanced performance in other non-electrochemical devices, such as resistive-type gas sensors, or applications such as gas separation, that rely on or utilize gas adsorption or catalytic reactions for some purpose.

According to embodiments of the present invention, an electric field can be used to alter gas adsorption and chemical reactions for various applications. The electric field may be generated when a voltage is applied between (at least) two surfaces. Also, multiple voltages may be applied. None of these surfaces needs be local to the device. One of the surfaces may be ground. A conductive element that is purposefully biased with the applied voltage so as to generate an electric field can be called an "electric-field electrode".

An indirectly-generated, external electric field is created in a way which does not result in the passage of current (electronic or ionic) through a device. In the indirectly-generated electric field, current is blocked by an insulator as in the case of a capacitor and by material that does not conduct ions.

A directly-generated electric field, however, is created when a metal or semiconductor has a voltage directly applied to it, whereby electrical current flows through the material. This is also the case when an electrochemical cell is directly biased, except that, at the interface between the electrolyte and metal or semiconductor electrode, the current provides electrons for the electrochemical reaction to occur rather than passing through the device.

In the case of an electrochemical cell, an indirectly-generated electric field does not result in charge reaching the electrolyte or electrodes making up the cell. However, a directly-generated field provides charge to the interface of the metal or semiconductor and the electrolyte.

According to certain embodiments of the present invention, other parts of the device or catalyst support may participate, either directly or indirectly, in the generation of the electric field. An example of direct participation is where voltage or current is directly applied to a cell as in case of NEMCA. An example of indirect participation is where "natural" field exists in the material.

Embodiments of the present invention provide active shaping of an electric field. During active shaping, the electric field distribution may be made uniform or non-uniform, and may be effectively and actively "shaped" to any desired (contour) profile with respect to specific locations on the device or catalyst support (e.g., local reaction zones) or to the entire device/support. The electric fields may be perpendicular, parallel, or any angle in between, with respect to the local reaction zones or the entire device/support. The electric fields may also penetrate any point within the device. Furthermore, the field strengths at various points in the device/support may differ.

Electric-field electrodes may be placed in any number and/or arrangement around local reaction zones or the entire device/support. Single or multiple "electric-field electrodes" may be used at any given time. Different layer materials may be used for different "electric-field electrodes" for compatibility with surrounding materials. The "electric-field electrodes" may be provided as single or multiple instances of insulation, conduction, and cap layers. The number of each layer type for a given "electric-field electrode" need not be the same as the number of layers in other "electric-field electrodes". The "electric field electrodes" may be imbedded in or on the surface of a device. The "electric field electrodes" may exist in specially designed cavities within the device/support and may incorporate gaps between segments.

The insulation layer for an electric-field electrode acts as a barrier to charge (i.e., electronic or ionic) flow through areas of a device, catalyst, or catalyst support (i.e., substrate holding catalyst) where such current is undesired. The layer may, but need not, participate in chemical and/or electrochemical reactions.

The conduction layer of an electric-field electrode acts as a pathway for the charge to reach the (blocking) insulation layer from the source of charge (e.g., power supply). The conduction layer may, but need not, participate in chemical and/or electrochemical reactions. The conduction layer may be formed of conducting materials such as gold (Au).

The cap, or cover, layer of an electric-field electrode acts to keep gas from adsorbing on the conduction layer of an electric-field electrode. The cap layer also acts to further (mechanically) secure conduction layer and insulation layer to substrate. The cap layer may, but need not, participate in chemical and/or electrochemical reactions. The cap layer may, but need not, be formed of insulating materials.

An electric-field electrode may take the form of any geometry such as a square or a circle, including variations in thickness and other dimensions. The geometry of the various layers of the electric-field electrode and layer types may, but need not, be different from each other.

The charge applied to any given "electric-field electrode" may be positive or negative. an "electric-field electrode" may alternatively be grounded or left floating. The electric field "direction" may be altered by changing the location of positive or negative charges, or by changing which "electric-field electrodes" are grounded or left floating.

A fixed (DC) voltage of any magnitude or sign may be applied to the "electric-field electrodes". The fixed voltage at "electric-field electrodes" may differ from or may be the same as all (or some) of the other "electric-field electrodes". For any given "electric-field electrode" the applied voltage may be switched between "constant" or "pulsed" biasing schemes. For any given "electric-field electrode" the applied voltage may be switched between "constant" (DC voltage) and (AC voltage) biasing schemes.

Pulsed (DC voltage) electric fields may be generated at different points in time with fixed or varying amplitude and period. In this scheme, the electric fields are pulsed by applying and removing the applied (DC) voltage(s) from all or some of the "electric-field electrodes". The period and/or amplitude of the pulses may, but need not, be the same for the different "electric field electrodes". For any given "electric-field electrode" the applied voltage may be switched between "pulsed" or "constant" biasing schemes. For any given "electric-field electrode" the applied voltage may be switched between "pulsed" (DC voltage) and (AC voltage) biasing schemes.

In some embodiments, a time-varying (e.g., sinusoidal) voltage may be applied to the "electric-field electrodes". For any given "electric-field electrode" the applied voltage may be switched between (AC voltage) and (DC voltage) biasing schemes.

Current and voltage of any "electric field electrode" may be measured by various means at any time to ensure that they continue to work during operation of device or catalyst.

By manipulating the electric field using electric-field electrodes according to embodiments of the present invention, certain mechanisms can be taken advantage of for enhanced performance in catalysis and solid state devices involving gases. The electric field enhancement may result in changes to the frequencies of the molecular bending modes of intramolecular adsorbate bonds or surface-adsorbate bonds. These electrostatic mechanisms can result in changes to bond angles and or bond lengths. In addition, polarization and resultant stabilization, alignment, or changes in orientation of the surface atoms or bulk atoms or in adsorbates (which may be polar species) may also occur.

Chemical mechanisms can include modification of orbitals and in the amount of donation/backdonation. There may be changes in the electron density of the surface and/or adsorbate and changes in the Pauli Repulsion, which may affect stability of complex formation (for charged and uncharged species). These chemical mechanisms may change the strength of intramolecular adsorbate bonds or surface-adsorbate bonds.

In some instances the electric field may result in both electrostatic and chemical mechanisms. There may be equal contribution by both mechanisms, or one may be more dominant than the other. In addition, both the electrostatic and chemical mechanisms may also alter lateral interactions between adsorbates in an adlayer.

In other instances the electric-field may cause changes to the Fermi level(s) of the material(s) involved in the device or process, thereby changing the adsorptive and/or catalytic properties of some or all of the materials.

The resulting changes to a system after the electric-field enhancement may cause several different effects. One effect is the altering of reaction pathways. For example, new reaction pathways may become available as a result of the electric-field enhancement. This may allow improvements in catalytic rates, byproduct concentrations, or new byproducts altogether. The kinetics of a reaction may be shifted to open new reaction pathways, or lower (or raise) the required temperature for reactions to occur.

Another effect is the altering of adsorption/desorption or dissociative/recombinative processes. For example, the adsorption of reaction inhibitors (or "poisons") may be prevented from accumulating or caused to desorb in a desirable way. Reaction promoters (e.g., co-adsorbates that enhance reactions) may be attracted by the electric-field to each other or specific reaction sites. In addition, desired reactions may speed up or undesirable reactions may slow down. The electric-fields may affect the temperatures at which these processes occur and may stabilize or destabilize these processes.

Surface relaxations or reconstructions may be shifted to lower (or higher) temperatures. Old relaxation/reconstruction processes may be prevented or new ones may be made available. In an embodiment, "electric field electrodes" may be used to prevent phase reconstruction by renewing the surface with, for instance, oxygen species that were lost as a result of poisoning, and subsequently resulted in new surface phases being formed.

The electric field enhancement may speed up or slow down diffusion of certain species, resulting in changes to a reaction. The collision of gas molecules from the gas phase may also be changed if the electric field has long-range effects; this may alter the way a reaction proceeds.

The electric field may result in changes to the thermodynamics of a system, which often times plays an important part in how reactions proceed. In devices or applications where the reactions depend on the thermodynamics of various species or complexes, the "electric-field electrodes" can shift the equilibrium to achieve new reactions and/or complexes, or to change the temperature at which such reactions occur.

In addition, it may be possible to affect the gas phase in such away that the processes mentioned above are altered.

Accordingly, the electric field generated with the "electric-field electrodes" can be effectively "shaped" to produce the desired field profile in the device/support or at specific locations in the device/support. Furthermore, the shaped electric field may be actively changed with time if desired.

The electric field generated with the "electric-field electrodes" may be used to purposefully (or unintentionally) "force" adsorption, desorption, or specific reactions.

The electric field generated with the "electric-field electrodes" may be used to reverse the effects of poisoning by inhibitors.

The electric field generated with the "electric-field electrodes" may be used to attract reaction promoters.

The electric field generated with the "electric-field electrodes" may be used to enhance performance in electrochemical devices, (e.g., gas sensors and fuel cells), non-electrochemical devices (e.g., gas sensors which do not utilize an electrolyte), and in general catalytic reactions (e.g., ethylene oxidation) or electrochemically-enhanced (i.e., NEMCA) reactions.

The electric-field electrodes may be used to improve such features as sensitivity, selectivity, and response time in a gas sensor. The "electric-field electrodes" may be incorporated into a gas sensor array, which has other performance enhancing features, such as imbedded heaters, etc. The gas sensor array may have multiple numbers of electrodes and may be used to detect a multitude of gases. The sensing electrodes in such a gas sensor array may be in the same gas environment and may, but need not, include an air-reference or other type of reference electrode.

In an electrochemical system, localized fields exist around a region known as the dipole layer. This region is important for the way in which electrochemical reactions occur in such systems. By using the external electric-field generated with the "electric-field electrodes", these "natural" electric fields may be altered. Direct control of the field can result in desirable changes to the system. NEMCA can be limited in the control of the electric field that results from a direct bias, as increased direct biases can result in Joule heating and/or decomposition of the electrolyte or electrodes. However, the limit of the electric field produced with the "electric field electrodes" is likely many orders of magnitude higher.

"Electric-field electrodes" can be used in a gas sensor to change sensitivity, selectivity, and response time of the device. "Electric-field electrodes" can also be used to alter catalytic reactions as demonstrated by their effects on the gas composition coming off the device and species that exist at the device surface.

Certain embodiments of the present invention can involve potentiometric, impedancemetric (resistive and/or capacitive), or amperometric gas sensors.

Figure 1B:
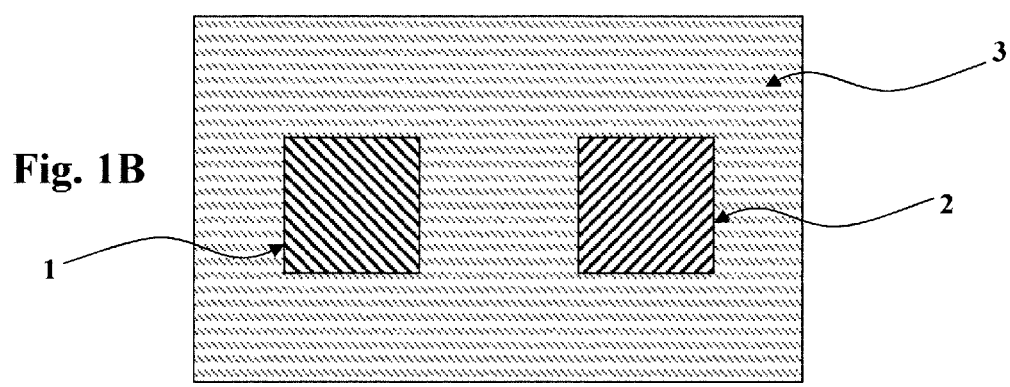
Figure 1C:
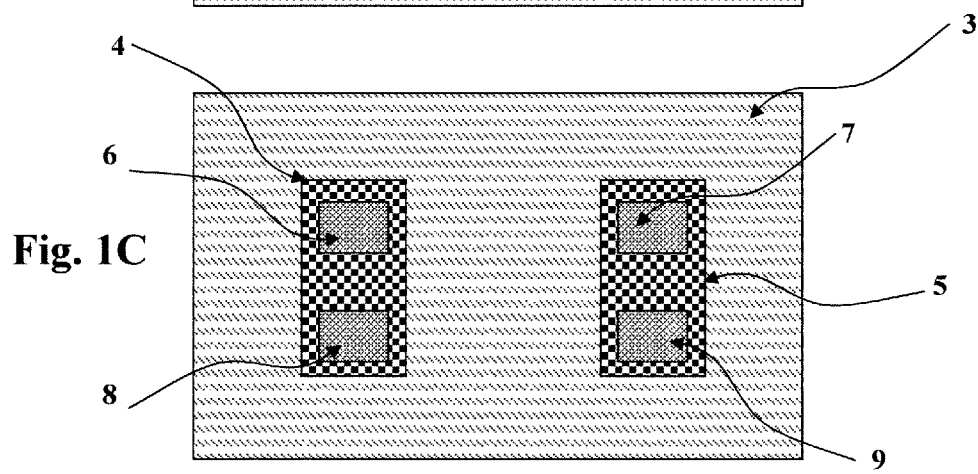

FIGS. 1A-1C show an embodiment for applying an electric field using electric field electrodes that are parallel to the sensing electrodes of a gas sensor. Referring to FIG. 1A, which shows a cross-section of the parallel-field embodiment for gas sensor applications according to an embodiment of the present invention, sensing electrodes 1 and 2 can be attached to substrate 3. The substrate 3 can be an electrolyte or other material. In a specific embodiment where the substrate 3 is formed of electrolyte, the substrate can be formed of yttria stabilized zirconia (YSZ). In one embodiment, the sensing electrodes 1 and 2 can be formed of the same material. However, in other embodiments, the sensing electrodes 1 and 2 can be formed of different materials. For example, in a specific embodiment, the first sensing electrode 1 can be formed of $La_2CuO_4$, and the second sensing electrode 2 can be formed of platinum (Pt). An electrochemical cell is formed when the first electrode 1 and second electrode 2 are in contact with the substrate 3, when substrate 3 is an electrolyte The sensing electrodes 1 and 2 can be provided in a single gas environment. On the opposite side of the solid electrolyte 3 from the first and second sensing electrodes 1 and 2, electric-field electrodes can be provided to apply a parallel electric field. A first electric-field electrode 6 and a second electric-field electrode 8 can be provided corresponding to the first sensing electrode 1. A third electric-field electrode 7 and a fourth electric-field electrode 9 can be provided corresponding to the second sensing electrode 2. In a specific embodiment, a first insulator 4 can be provided beneath the first and second electric-field electrodes 6 and 8 and the solid electrolyte 3, and a second insulator 5 can be provided between the third and fourth electric-field electrodes 7 and 9 and the solid electrolyte 3. The first and second insulators 4 and 5 can be formed of, for example, $Al_2O_3$. The electrodes of the electric-field electrodes can be formed of a conductive material. For example, the electrodes can be formed of gold (Au). A cap layer can be provided on each of the electric-field electrodes for insulation and improved adhesion. The cap layers can be formed of, for example, $Al_2O_3$. The insulation layers 4 and 5 can allow the conduction layers of the electric-field electrodes 6 and 7 to not make contact with substrate 3. If substrate 3 is selected to be an electrolyte, then insulation layers 4 and 5, and conduction layers 6 and 7, are not considered part of the electrochemical cell.

FIG. 1B shows the top surface of the parallel-field embodiment shown in FIG. 1A, with sensing electrode 1 and electrode 2 positioned on the substrate 3. Metallic leads or other metallization (not shown) can be attached to the sensing electrodes in many ways. For the sensor application these leads can be used to transmit information about the electromotive field (EMF) at the electrode to a measurement device.

FIG. 1C shows the bottom surface of the parallel-field embodiment shown in FIG. 1A, with insulation layer 4 and conduction layers 6 and 8 making up two "electric-field electrodes." Metallic leads (not shown) can be attached to the electric-field electrodes in many ways.

Different "charging schemes" may be used to get variations in the gas sensor sensitivity, selectivity, response time, etc. This is done by accumulating positive (+) or negative (−) charge via an applied voltage at any of conduction layers 6 through 9.

As shown in Table 1 below, there are a number of different "charging schemes" each one resulting in a different electric-field distribution in the device, and hence a different modification of the sensor behavior.

TABLE 1

| # | Conduction layer 6 | Conduction layer 7 | Conduction layer 8 | Conduction layer 9 |
| --- | --- | --- | --- | --- |
| 1 | + (−) charge | floating | floating | floating |
| 2 | + (−) charge | + (−) charge | floating | floating |
| 3 | + (−) charge | + (−) charge | + (−) charge | + (−) charge |
| 4 | + (−) charge | − (+) charge | + (−) charge | − (+) charge |
| 5 | + (−) charge | + (−) charge | − (+) charge | − (+) charge |
| 6 | + (−) charge | ground | floating | − (+) charge |
| 7 | Etc. | Etc. | Etc. | Etc. |

As discussed herein, the electric-field electrodes may be used to "shape" the field profile in a device. This technique was tested in a gas sensor device and modeled to show how the field profile may change during "shaping."

Figure 2A:
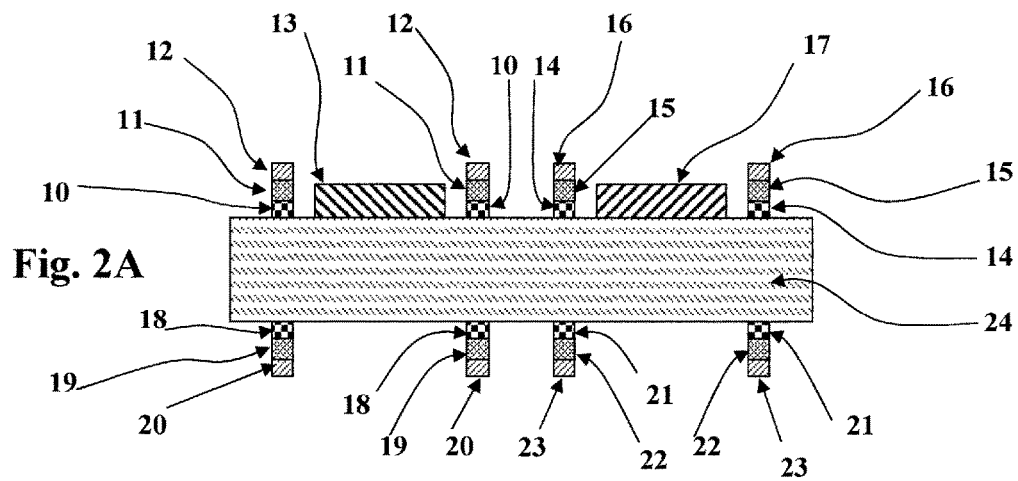
FIGS. 2A-2C show a planar gas sensor according to an embodiment of the present invention.
Figure 2B:
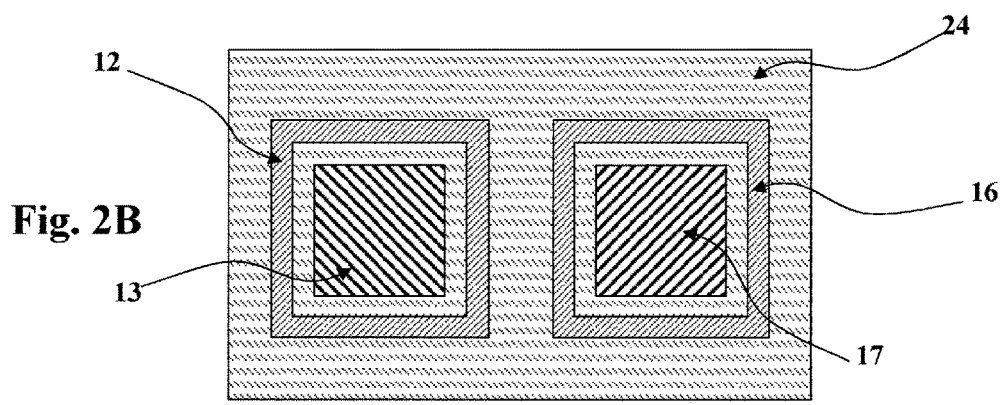
Figure 2C:
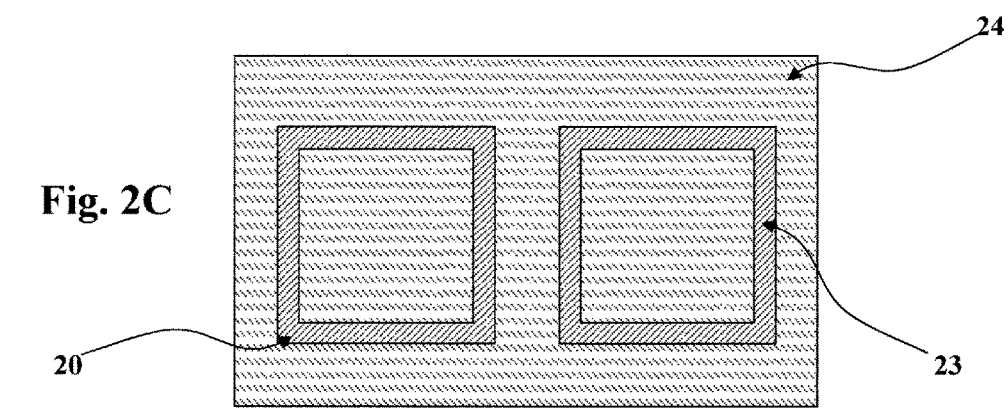

FIGS. 2A-2C show an embodiment for applying a shaped electric field to sensing electrodes of a planar gas sensor.

Referring to FIG. 2A, which shows a cross-section of the shaped-field embodiment for gas sensor applications, sensing electrodes 13 and 17 can be attached to a substrate 24. The substrate 24 can be an electrolyte or other material. In a specific embodiment where the substrate 3 is formed of electrolyte, the substrate can be formed of YSZ. As described with respect to the embodiment illustrated in FIGS. 1A-1C, the sensing electrodes can be formed of the same or different material. For example, the first sensing electrode 13 can be formed of $La_2CuO_4$ and the second sensing electrode 17 can be formed of Pt. If substrate 24 is an electrolyte, then the first sensing electrode 13, second sensing electrode 17, and the substrate 24 make up an electrochemical cell. The sensing electrodes 13 and 17 can be provided in a single gas environment.

Electric-field electrodes can be provided at positions on the solid electrolyte 24 to apply an actively shaped electric field. A first electric-field electrode 11 can be provided in a ring shape around the first sensing electrode 13, and a second electric-field electrode 15 can be provided in a ring shape around the second sensing electrode 17. A third electric-field electrode 19 can be provided on the opposite side of the solid electrolyte 24 from the first sensing electrode 13 and in a ring shape corresponding to the first electric-field electrode 11, and a fourth electric-field electrode 22 can be provided on the opposite side of the solid electrolyte 24 from the second sensing electrode 17 and in a ring shape corresponding to the second electric-field electrode 15. In a specific embodiment, a first insulator 10 can be provided in a ring shape between the first electric-field electrode 11 and the solid electrolyte 24, a second insulator 14 can be provided in a ring shape between the second electric-field electrode 15 and the solid electrolyte 24, a third insulator 18 can be provided in a ring shape between the third electric-field electrode 19 and the solid electrolyte 24, and a fourth insulator 21 can be provided in a ring shape between the fourth electric-field electrode 22 and the solid electrolyte 24. The first, second, third and fourth insulators 10, 14, 18 and 21 can be formed of, for example, $Al_2O_3$. The electrodes of the electric-field electrodes can be formed of a conductive material. For example, the electrodes can be formed of gold (Au).

A cap layer can be provided on each of the electric-field electrodes for insulation. In a specific embodiment, a first cap layer 12 can be provided on the first electric-field electrode 11, a second cap layer 16 can be provided on the second electric-field electrode 15, a third cap layer 20 can be provided on the third electric-field electrode 19, and a fourth cap layer 23 can be provided on the fourth electric-field electrode 22. The cap layers can be formed of, for example, $Al_2O_3$. The cap layer may be omitted if desired. Metallic leads or other metallization (not shown) may be sandwiched between the individual conduction layers and cap layers. The conduction layers of the electric-field electrodes do not make contact with substrate 24, though if desired the cap layer can do so. If substrate 24 is an electrolyte, then layers 10 through 12, 14 through 16, 18 through 20, and 21 through 23 are not part of the electrochemical cell.

FIG. 2B shows a top surface of the shaped-field embodiment, with sensing electrode 13 and electrode 17 attached to substrate 24. Metallic leads or other metallization (not shown) can be attached to the sensing electrodes in many ways. For the sensor application these leads are used to transmit information about the EMF at the electrode to a measurement device. Multiple sensing electrodes and "electric-field electrodes" may be incorporated into such a device as well, making it a gas sensor array.

FIG. 2C shows a bottom surface of the shaped-field embodiment, with insulation layers 10, 14, 18, and 21, and conduction layers 11, 15, 19, and 22 making up four electric-field electrodes. Metallic leads (not shown) can be attached to an "electric-field electrodes" (making contact with the conduction layers) in many ways. These electric-field electrodes may also have geometries that are different from a ring-shape; in fact the sensing (or other active material) may be formed in a ring with the electric field electrode in arranged in the center. Different "charging schemes" may be used to get variations in the gas sensor sensitivity, selectivity, response time, etc. This is done by accumulating positive (+) or negative (−) charge via an applied voltage at any of conduction layers 11, 15, 19, and 22.

As shown in Table 2 below, there are a number of different "charging schemes" each one resulting in a different electric-field distribution in the device, and hence a different modification of the sensor behavior. Charging schemes 1 through 3 were tested using the shaped-field embodiment. Note, in charging scheme 6, conduction layers 11 (and 19) and 15 (and 22) have different charge values (i.e., the voltage applied to each is of a different magnitude). The other schemes are possible but have not been tested yet; they are included to show the advantages of a "shaped field" device.

TABLE 2

| # | Conduction layer 11 | Conduction layer 15 | Conduction layer 19 | Conduction layer 22 |
|---|---|---|---|---|
| 1 | + (−) charge | + (−) charge | − (+) charge | − (+) charge |
| 2 | + (−) charge | − (+) charge | − (+) charge | + (−) charge |
| 3 | + (−) charge | floating | − (+) charge | floating |
| 4 | floating | + (−) charge | Floating | − (+) charge |
| 5 | + (−) charge ground | ground floating | − (+) charge | − (+) charge floating |
| 6 | ground | + (−) charge | + (−) charge | floating |
| 7 | + (−) charge 1 | + (−) charge 2 | − (+) charge 1 | − (+) charge 2 |
| 8 | Etc. | Etc. | Etc. | Etc. |

FIGS. 3A-3H illustrate the results from the shaped-field embodiment shown in FIGS. 2A-2C. The sensing electrodes 13 and 17 are $La_2CuO_4$ and Pt, respectively.

Figure 3A:
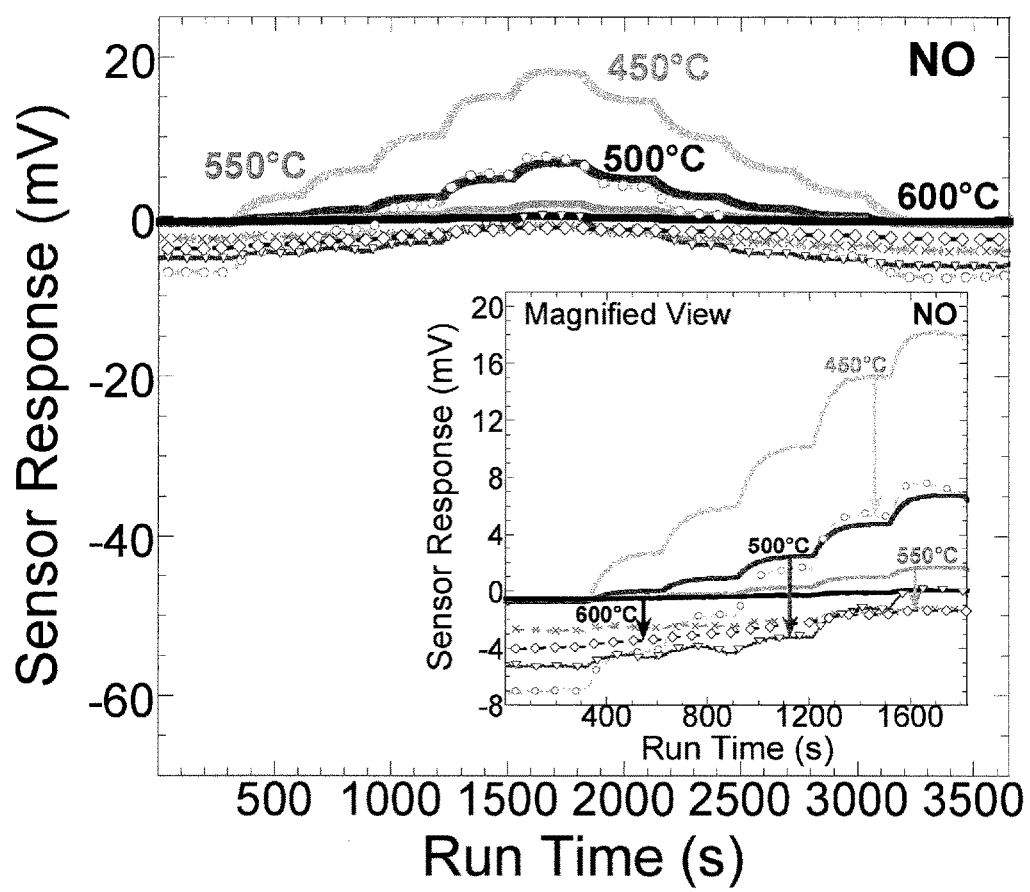
FIGS. 3A-3B show plots comparing changes in NO and $NO_2$ sensitivity with and without the use of the electric-field electrodes (bias scheme 1, Table 2) for a variety of ambient temperatures.

FIG. 3A represents the (potentiometric) NO sensor results from the shaped-field embodiment shown in FIGS. 2A-2C. The sensing electrodes are Pt and $La_2CuO_4$, which were exposed to the same gas environment (i.e., no air-reference). This plot compares the conditions with no electric field to those with a +1V bias using charging scheme 1 at 450 C, 500 C, 550 C, and 600 C. In the experiment represented in this figure, the top electric-field electrodes (surrounding the Pt and $La_2CuO_4$ sensing electrodes) were positively biased. The corresponding "electric-field electrodes" on the opposite side of the substrate were both negatively biased. In other words, a voltage was applied between the top field electrodes (high potential) and the bottom field electrodes (low potential).

Figure 3B:
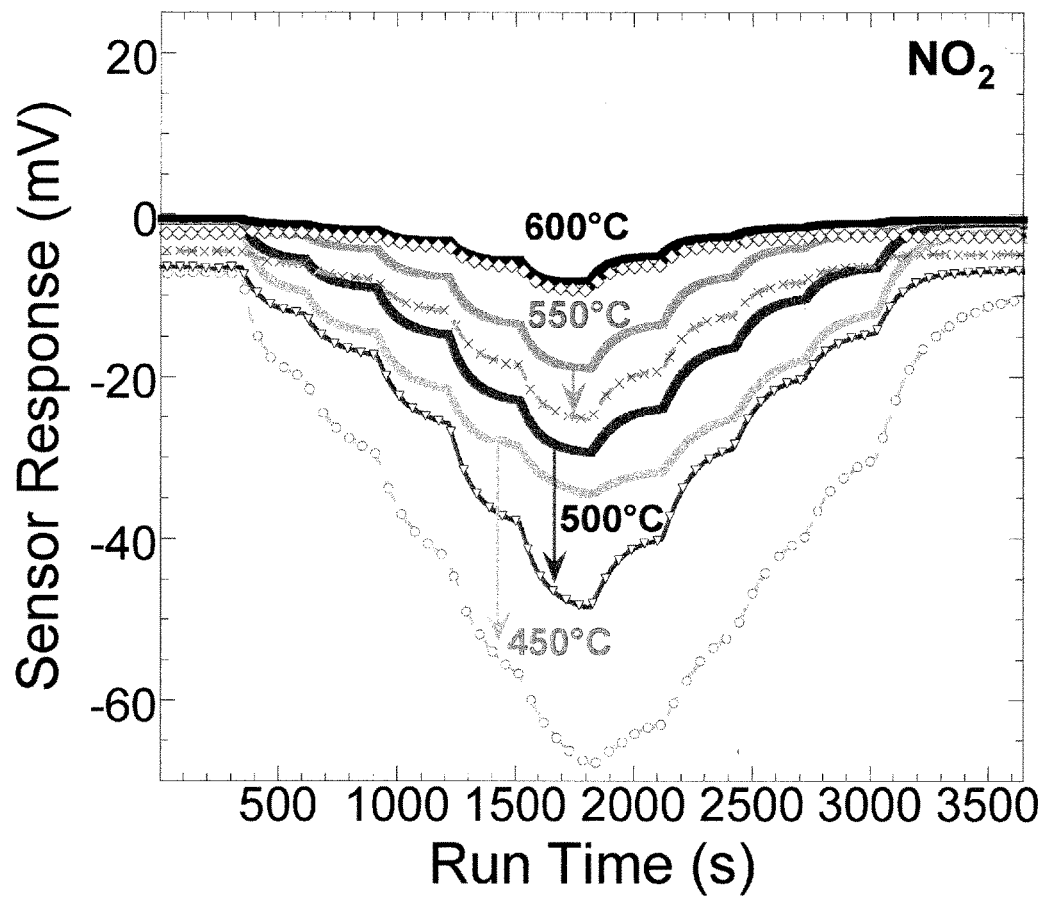

FIG. 3B represents the $NO_2$ sensor results from the shaped-field embodiment shown in FIGS. 2A-2C. The sensing electrodes are Pt and $La_2CuO_4$. This plot compares the conditions with no electric field to those with a +1V bias using charging scheme 1. In the experiment represented in this figure, the top electric-field electrodes (surrounding the Pt and $La_2CuO_4$ sensing electrodes) were positively biased. The corresponding "electric-field electrodes" on the opposite side of the substrate were both negatively biased.

Figure 3C:
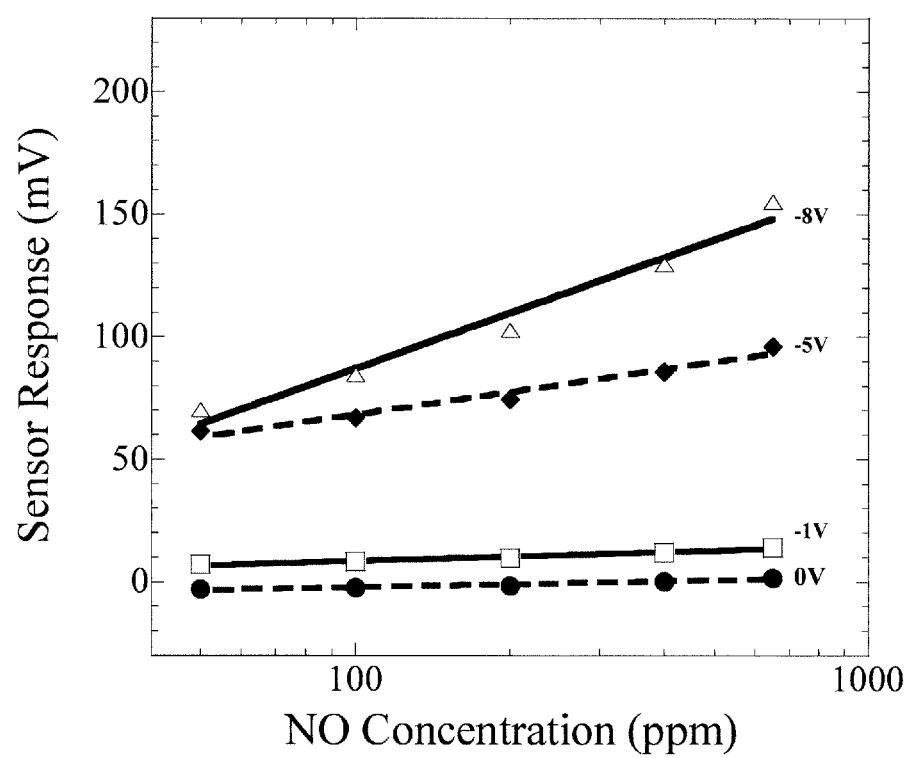
FIGS. 3C-3D show the results of NO and $NO_2$ sensitivity for biasing scheme 1 (Table 2) with negative (−) field bias at 500 C applied to the embodiment shown in FIGS. 2A-2C.

FIG. 3C shows the steady state sensor response of the shaped-field embodiment shown in FIGS. 2A-2C. In this case, charging scheme 1 (table 2) was used to apply negative (−) biases of different strength to top "electric field electrodes (surrounding the Pt and $La_2CuO_4$ sensing electrodes). The corresponding "electric-field electrodes" on the opposite side of the substrate were both positively biased.

Figure 3D:
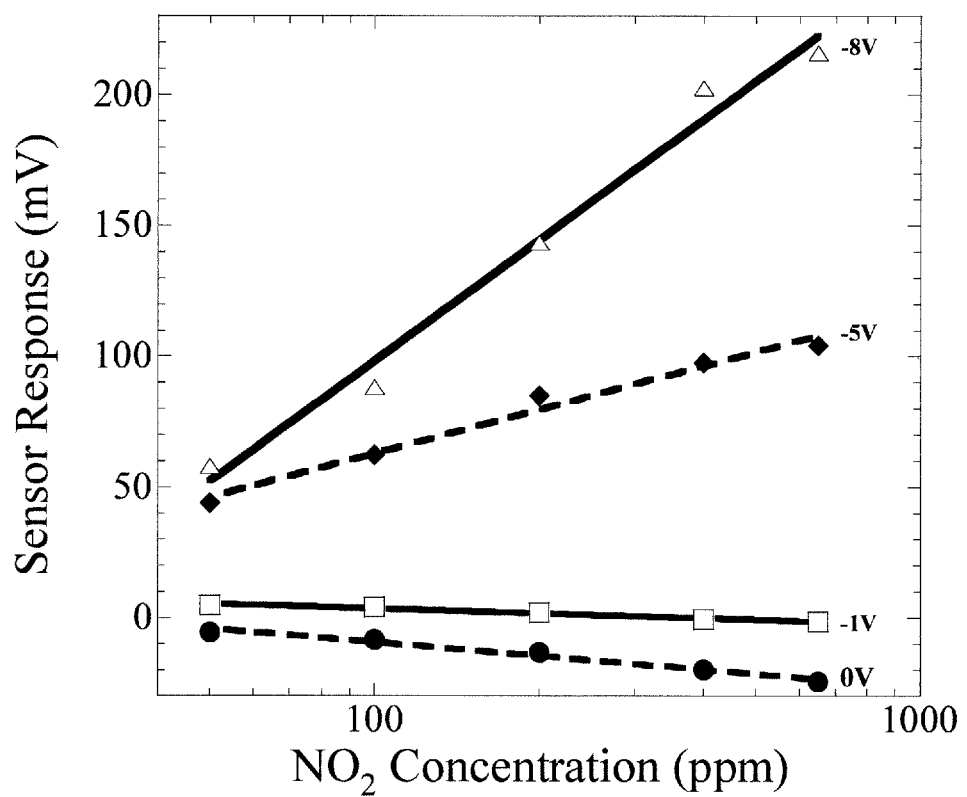
Figure 3E:
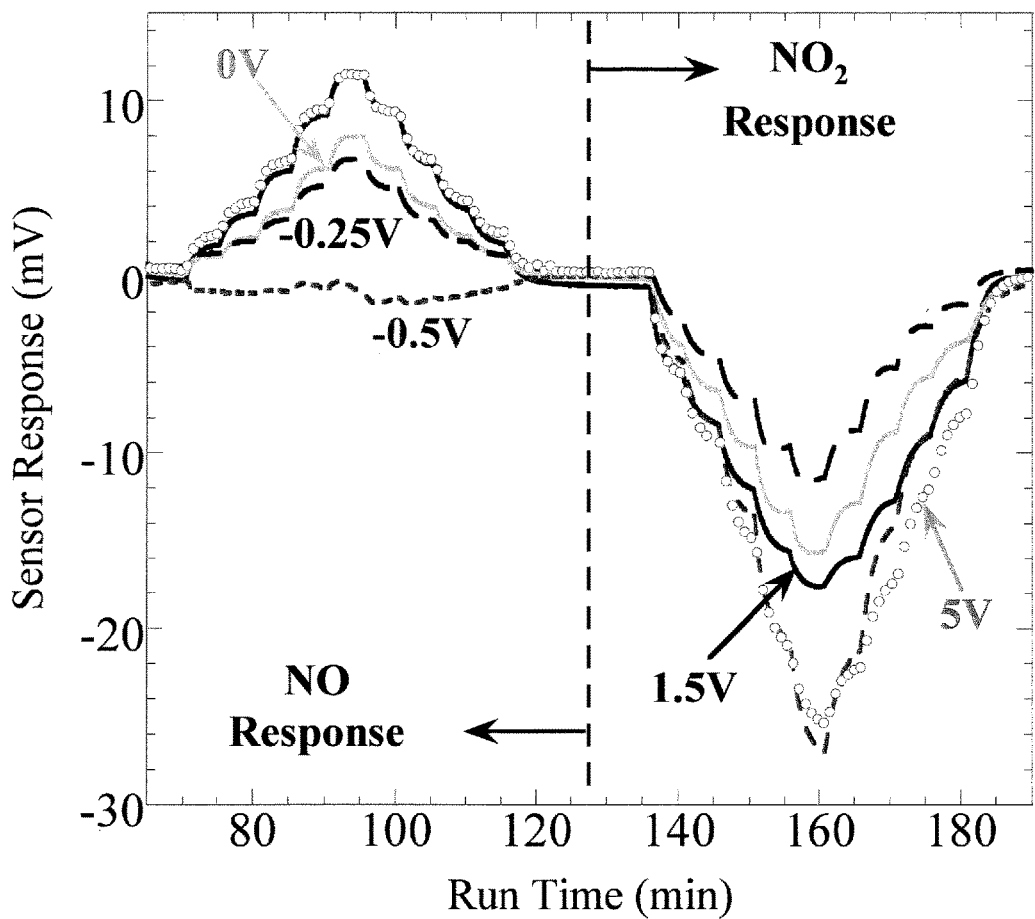
FIG. 3E shows the sensor response to NO and $NO_2$ at 500 C for biasing scheme 2 (Table 2) applied to the embodiment shown in FIGS. 2A-2C.

FIG. 3E shows the NO and $NO_2$ sensor response for biasing scheme 2 (Table 2) applied to the embodiment shown in FIGS. 2A-2C. In the cases marked as positive bias, a high potential) was applied to the electric field electrode surrounding the La2CuO4 sensing electrode (conduction layer 11) and at the electric field electrode on the opposite side of the substrate, aligned with the Pt sensing electrode (conduction layer 22). Simultaneously, a low potential was applied at the electric field electrode surrounding the Pt sensing electrode (conduction layer 15) and at the electric field electrode on the opposite side of the substrate, aligned with the La2CuO4 electrode (conduction layer 19). In cases marked as negative (−) bias, the high and low potentials applied at the electric field electrodes were reversed.

Figure 3F:
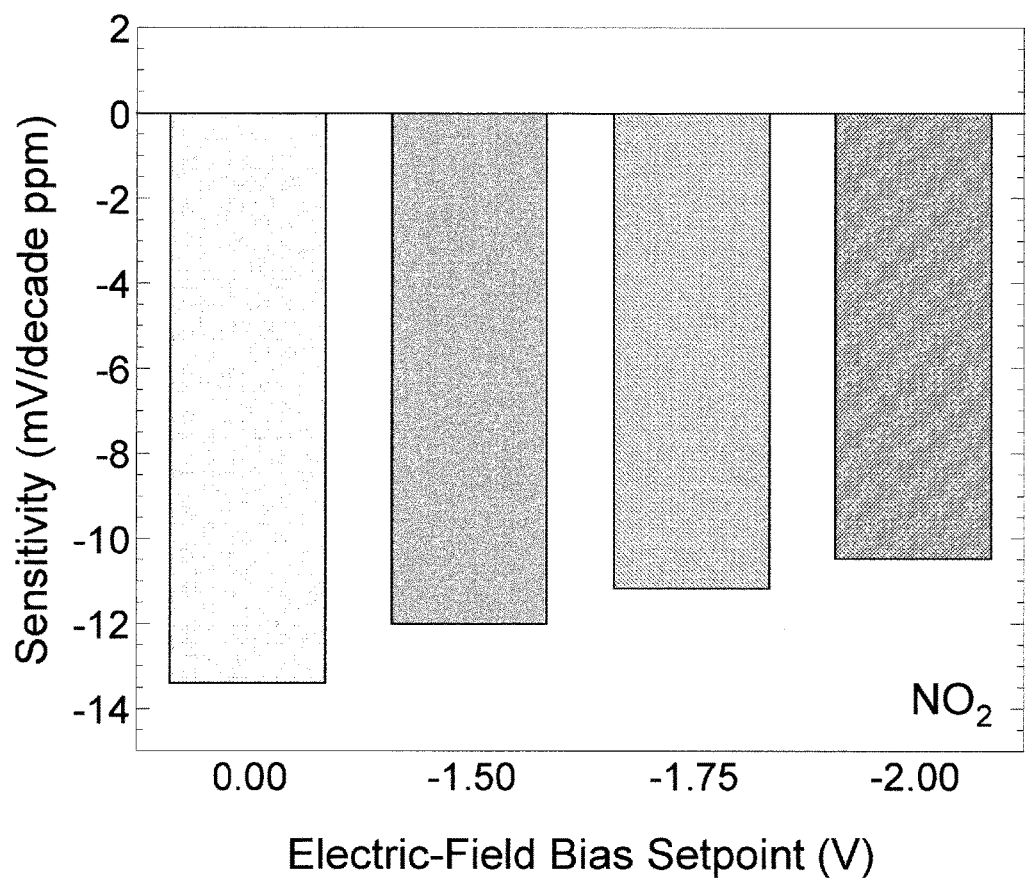
FIG. 3F shows $NO_2$ results for biasing scheme 3 (Table 2) applied to the embodiment shown in FIGS. 2A-2C, where only the conduction layers 11 and 19 on the $La_2CuO_4$ side of the device are charged; the other conduction layers are left uncharged.
Figure 3G:
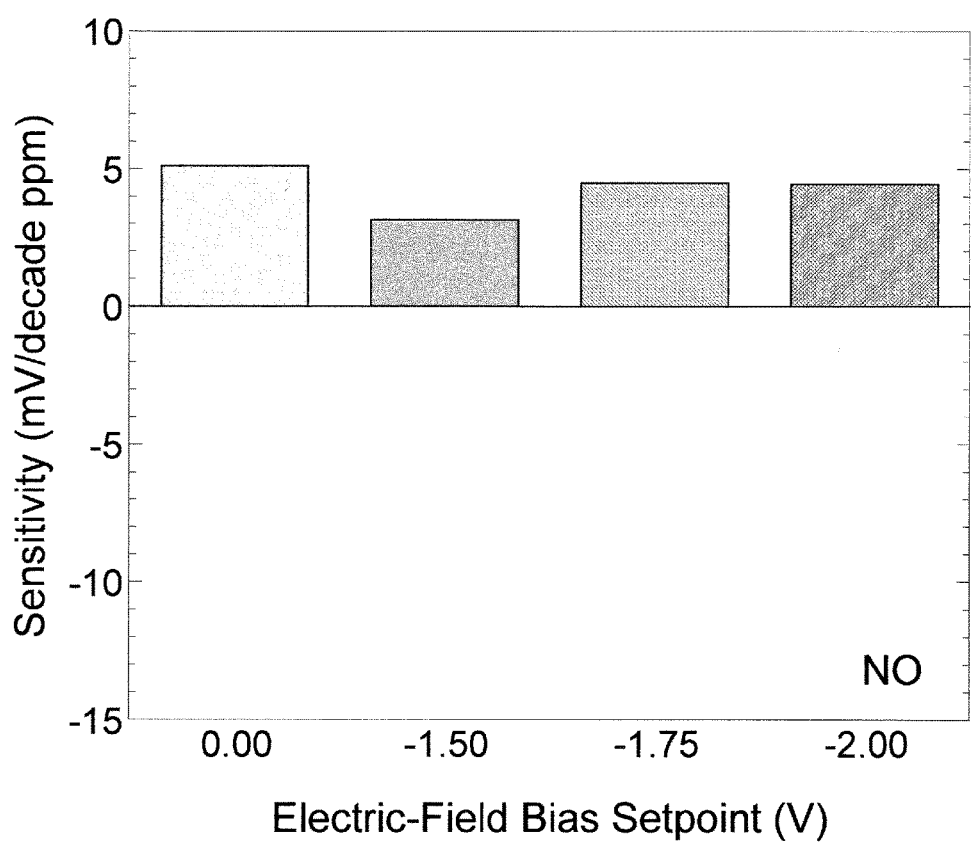
FIG. 3G shows NO results for biasing scheme 3 (Table 2) applied to the embodiment shown in FIGS. 2A-2C, where only the conduction layers 11 and 19 on the $La_2CuO_4$ side of the device are charged; the other conduction layers are left uncharged.

FIGS. 3F and 3G show the NO and $NO_2$ sensitivity results for biasing scheme 3 applied to the embodiment shown in FIGS. 2A-2C. In this case a negative bias was applied to the electric field electrodes (conduction layer 11) surrounding the La2CuO4 sensing electrode, with a positive bias applied to the corresponding electric field electrode on the opposite side of the substrate (conduction layer 19). The other two electric field electrodes (conduction layers 15 and 22), aligned with the Pt sensing electrode, were left unbiased (floating).

Figure 3H:
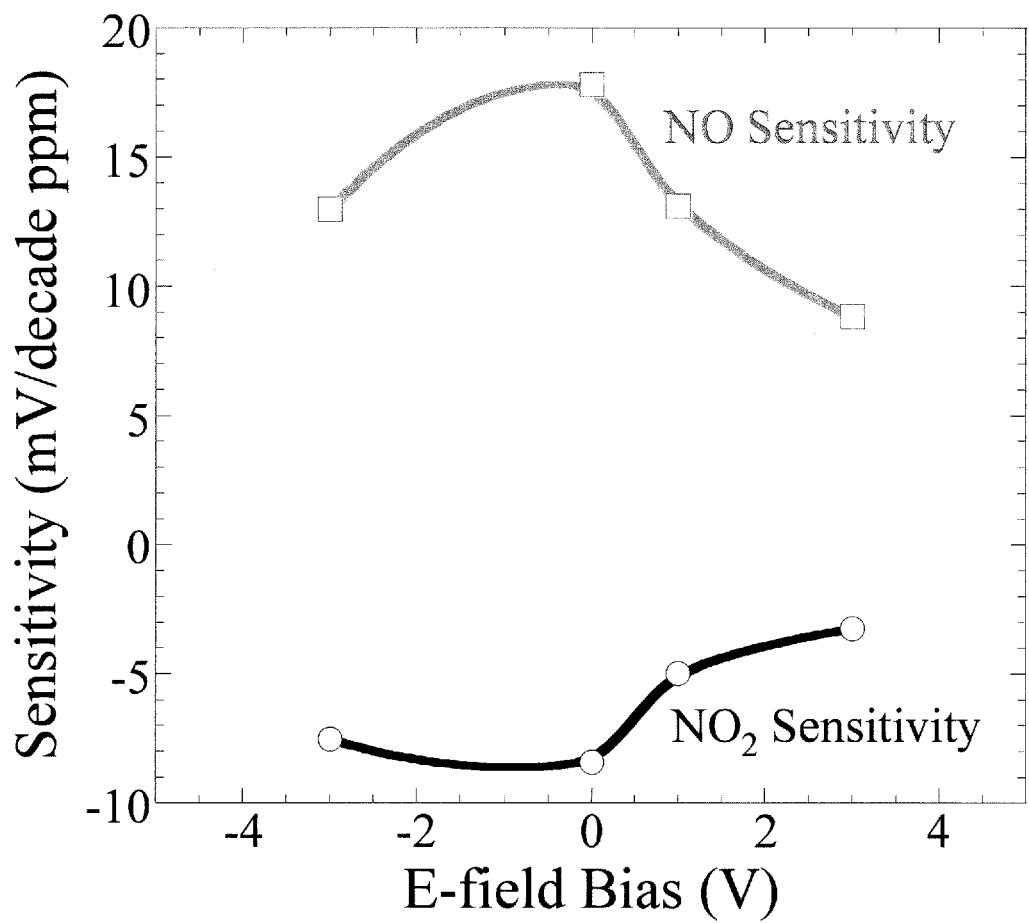
FIG. 3H shows the results for biasing scheme 4 (Table 2) applied to the embodiment shown in FIGS. 2A-2C.

FIG. 3H shows the NO and $NO_2$ sensitivity results for biasing scheme 4 applied to the embodiment shown in FIGS. 2A-2C. In this case a positive (or negative (−)) bias was applied to the electric field electrodes (conduction layer 15) surrounding the Pt sensing electrode, with a negative (or positive) bias applied to the corresponding electric field electrode on the opposite side of the substrate (conduction layer 22). The other two electric field electrodes (conduction layers 15 and 22), aligned with the La2CuO4 sensing electrode, were left unbiased (floating).

The use of the electric field electrodes in the various charging schemes from Table 2 with the embodiment shown in FIGS. 2A-2C, resulted in different sensing behavior for the gas sensor (FIGS. 3A-3H). As illustrated in FIG. 3A, for charging scheme 1 (Table 2), the sensor response to NO changed as the electric field bias of 1 V was applied. Furthermore, the magnitude of the changes was different as the ambient temperature varied. However, when compared to FIG. 3B, it is clear that the electric-field electrodes enhanced the NO2 response of the device by quite a bit more. The selective enhancement or reduction of the mechanisms that cause the sensor response can be very useful in a number of electrochemical devices, non-electrochemical devices, and other related processes. Charging scheme 1 (Table 2) resulted in extremely large (~20× increase in NO sensitivity and ~10× increase in $NO_2$ sensitivity) as shown in FIGS. 3C and 3D. Furthermore, the sensitivity to $NO_2$ starts off negative and trends towards zero sensitivity before achieving a positive response. At the same time, the NO response only becomes increasingly positive. Therefore, it is possible that NO selectivity over $NO_2$ can be achieved.

The use of charging scheme 2 shown in FIG. 3E demonstrates the capability of a shaped electric field to further enhance a gas sensor. In this case, a positive field bias resulted in an increased NO2 response with increased bias, with a slightly increased NO sensitivity but no additional changes as the bias increased. On the other hand, negative field biases, resulted in decreased NO sensitivity to almost zero, while maintaining NO sensitivity. In fact for the bias of −0.5 V to the electric field electrodes, the NO sensitivity was negligible while the $NO_2$ sensitivity actually increased.

As shown in FIG. 3F-3G, charging scheme 3 (Table 2) resulted in similar changes in both NO and NO2 sensitivity as the electric field bias was changed. This suggests that this charging scheme might be used for achieving an enhanced total-NOx sensor signal.

FIG. 3H further demonstrates the ability of the various shaped electric fields to enhance a device in a number of ways. In this case, the results indicate that the bias scheme may result in NO selectivity because the NO2 sensitivity trends toward zero while the NO sensitivity remains relatively unchanged. Furthermore, the fact that different results were achieved for each shaped field bias schemes suggests that similar enhancements can be used to improve other electrochemical devices, non-electrochemical devices, and other related processes.

Figure 4A:
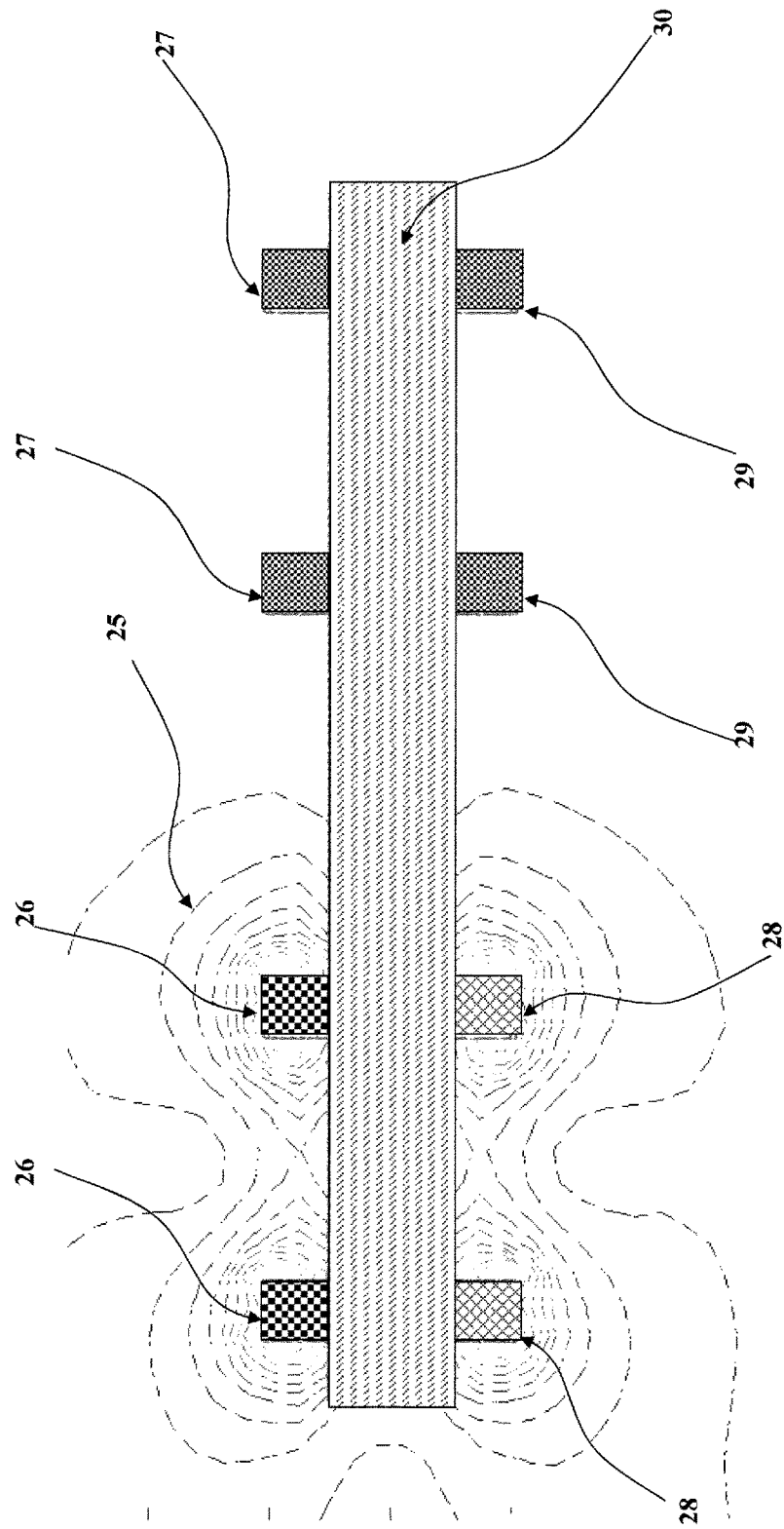
FIGS. 4A-4D show electric field plots of three different actively-shaped electric fields using the planar sensor according to the embodiment shown in FIGS. 2A-2C.

FIG. 4A is a representation of the electric-field contour map 25 showing relative field strengths for the shaped-field embodiment of FIGS. 2A-2C using charging scheme 3. Here, "electric-field electrode" 26 has a positive charge, while "electric-field electrode" 28 has a negative charge of equal magnitude. "Electric-field electrodes" 27 and 29 are left floating. Each contour 25 in the figure represents different field strengths moving away from the device surface and throughout the gas environment surrounding the device. While not shown, it should be noted that the field contours also extend through substrate 30 and other parts of device (i.e., the field penetrates the device).

Figure 4B:
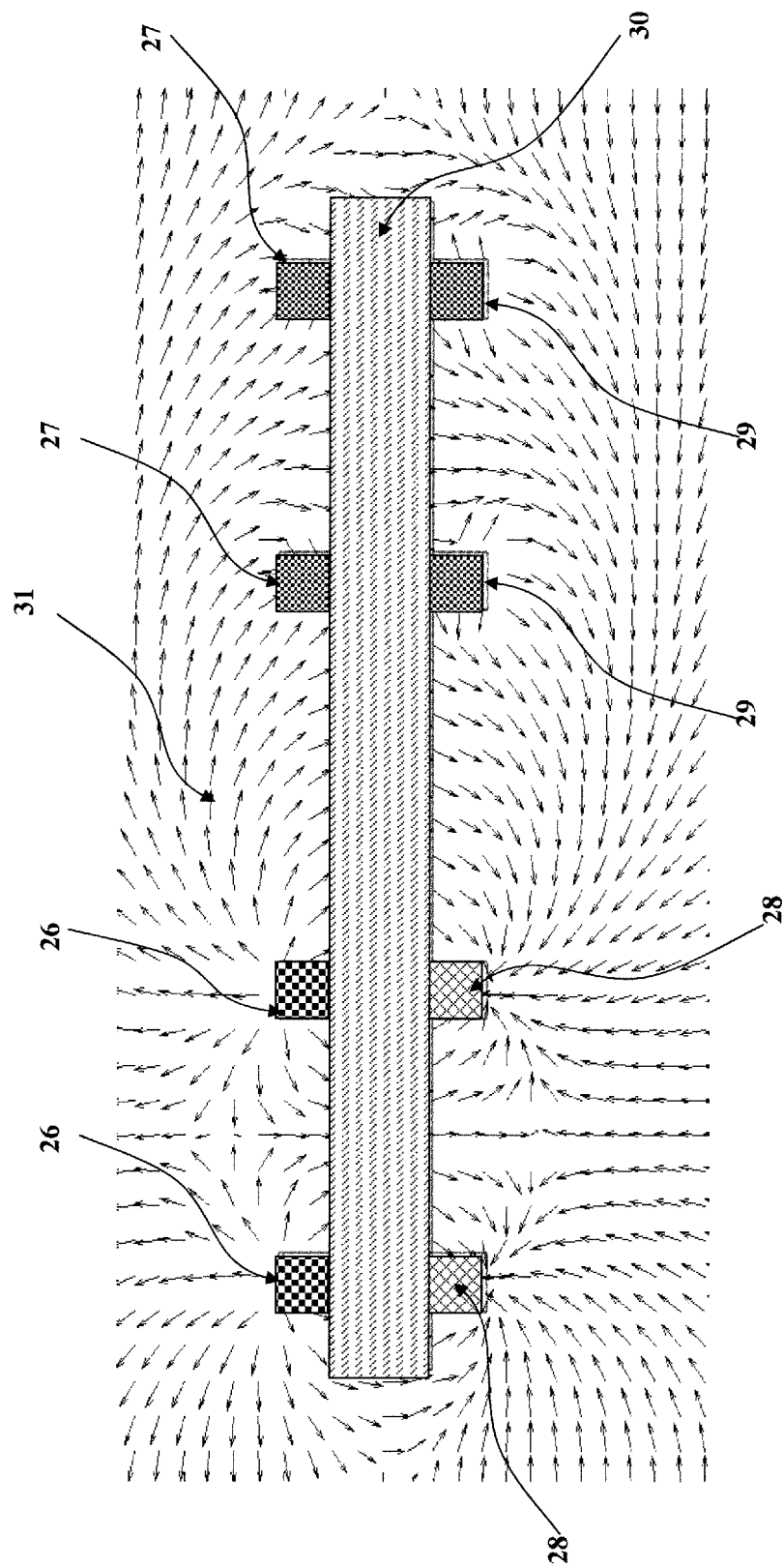

FIG. 4B is a representation of the electric-field vector map 31 for the same charging scheme as was presented in FIG. 4A. Each arrow in the figure represents the direction of the electric field in space. The electric field moves from regions of positive to negative charge. Looking at FIG. 4B and referring to FIG. 2B, it is clear that for this charging scheme (in the ideal case) the electric field is uniform near the center of the rings making up "electric-field electrodes" 26 and 28. However, the field is non-uniform near center of the rings for "electric-field electrodes" 27 and 29. The electric field contour map and electric field vector map in FIGS. 4A and 4B, will change depending on the values of several parameters (e.g., the voltage at the "electric-field electrodes" and/or the charging scheme used). While not shown, it should be noted that the field vectors also extend through substrate 30 and other parts of device (i.e., the field penetrates the device). Also, note that fringing effects near the edges of the "electric-field" electrodes have not been considered in the ideal case.

Figure 4C:
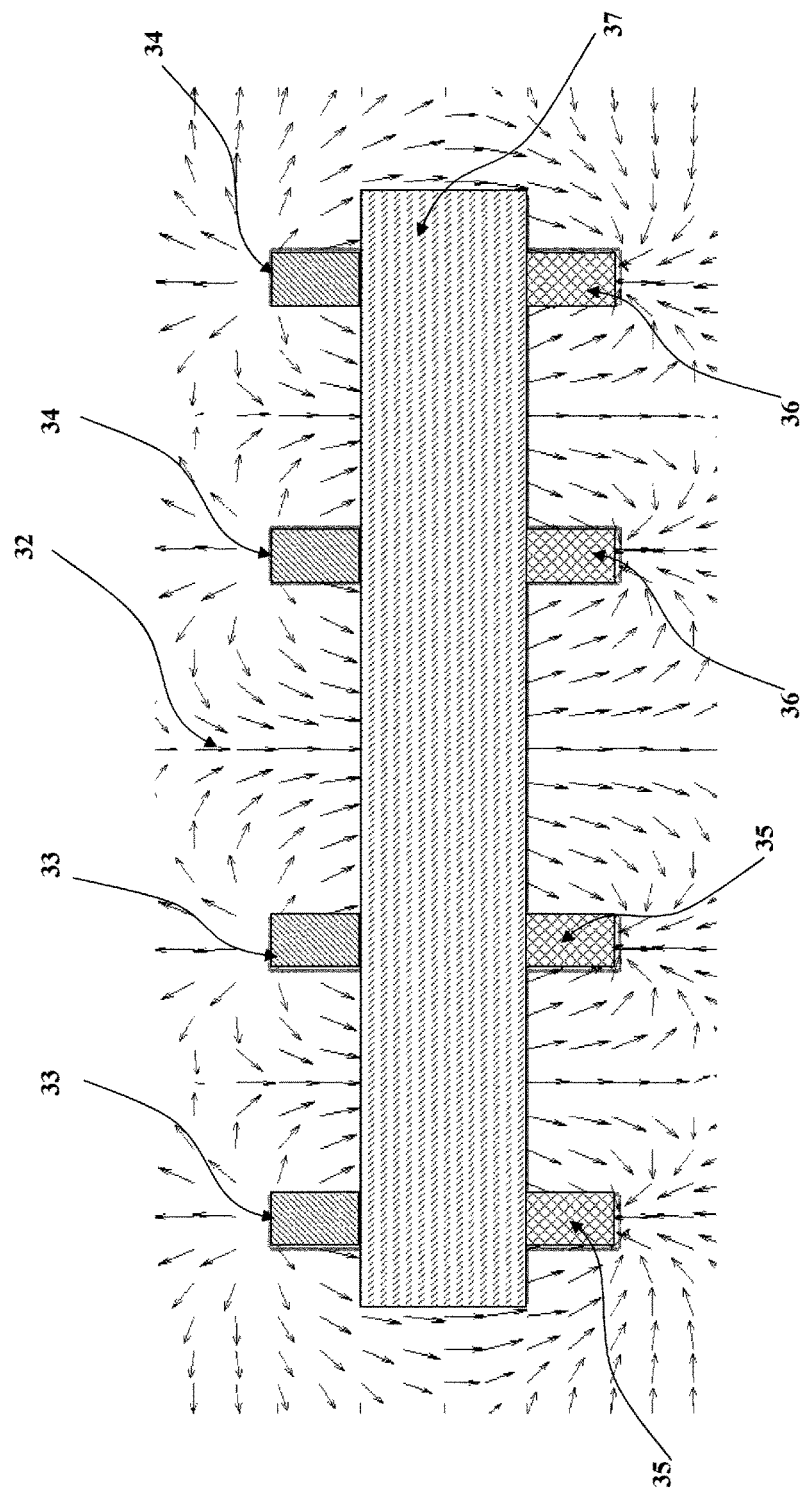

FIG. 4C is a representation of the electric-field vector map 32 for charging scheme 1 of the shaped-field embodiment in FIGS. 2A-2C. Here, "electric-field electrodes" 33 and 34 have a positive charge, while "electric-field electrodes" 35 and 36 have a negative charge. Looking at FIG. 4C and referring to FIG. 2C, it is clear that for this charging scheme (in the ideal case) the electric field is uniform near the center of the rings making up "electric-field electrodes" 33, 34, 35 and 36. Furthermore, the direction of the field vectors through the middle of the rings is the same for the left pair of rings (33 and 35) as it is for the right pair of rings (34 and 36). This is also the same direction as between the two pairs of rings (i.e., through the very middle of the device, perpendicular to the surface). Also note that the field distribution in this scheme is symmetric about the device and surrounding gas environment (assuming ideal case and no interference from neighboring objects). This electric field vector map will change depending on the values of the voltage at the "electric-field electrodes" (and if the charging scheme changes). While not shown, it should be noted that the field vectors also extend through substrate 37 and other parts of device (i.e., the field penetrates the device).

Figure 4D:
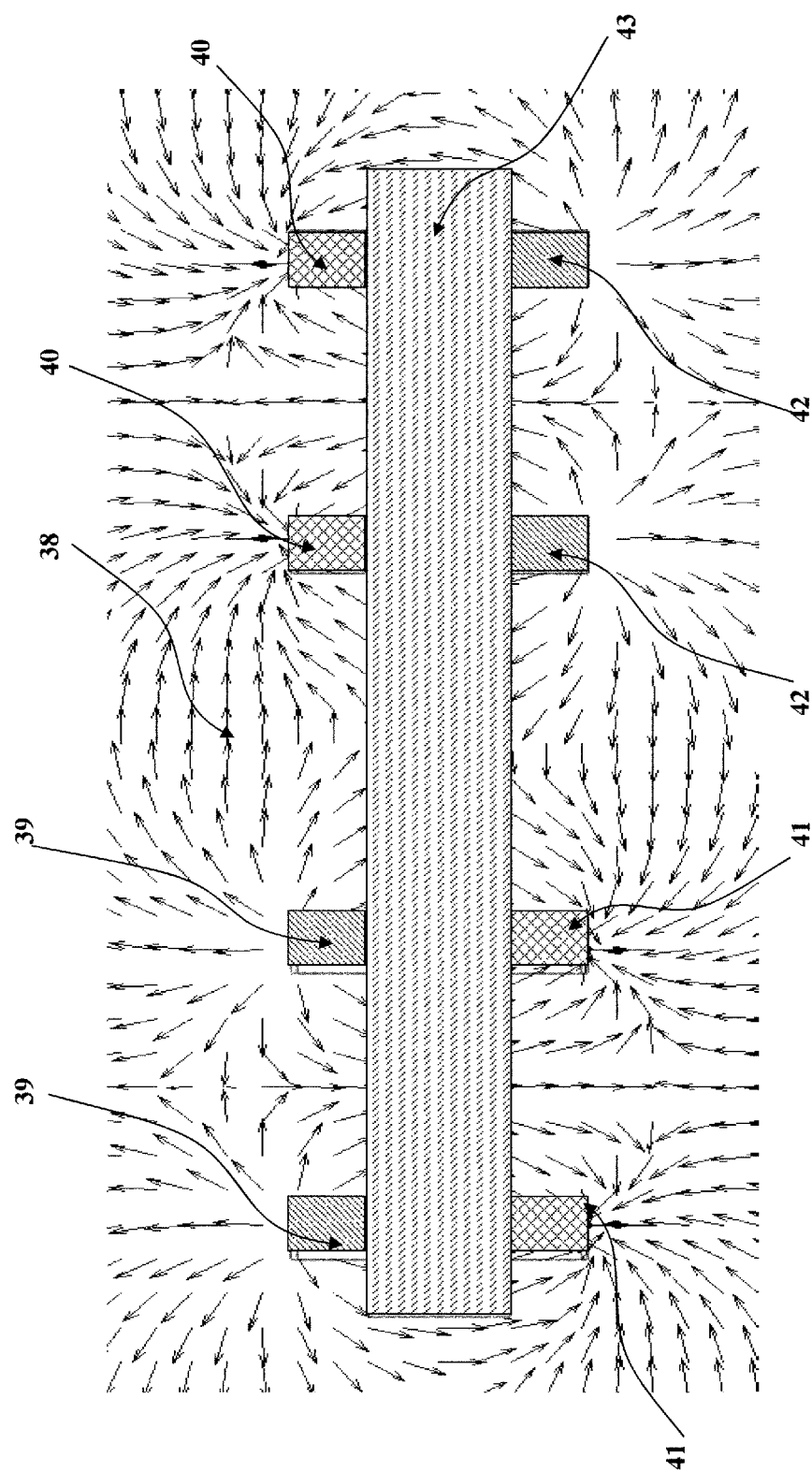

FIG. 4D is a representation of the electric-field vector map 38 for charging scheme 2 of the shaped-field embodiment in FIGS. 2A-2C. Here, "electric-field electrodes" 39 and 42 have a positive charge, while "electric-field electrodes" 40 and 41 have a negative charge. Looking at FIG. 4D and referring to FIG. 2C, it is clear that for this charging scheme (in the ideal case) the electric field is uniform near the center of the rings making up "electric-field electrodes" 39, 40, 41 and 42. Furthermore, the field vector direction through the middle of the rings is NOT the same for the left pair of rings (39 and 41) as it is for the right pair of rings (40 and 42); the directions are opposite each other (and perpendicular to the surface). Also note that the field distribution in this scheme is symmetric about the device and surrounding gas environment (assuming ideal case and no interference from neighboring objects). While this latter fact, mirrors the situation displayed in FIG. 4C, the field in between the two pairs of rings (i.e., at the very middle of the device) is no longer perpendicular to the surface; rather the field is now parallel to the surface. This electric field vector map will change depending on the values of the voltage at the "electric-field electrodes" (and if the charging scheme changes). While not shown, it should be noted that the field vectors also extend through substrate 43 and other parts of device (i.e., the field penetrates the device). Also, in addition to differences in the field vector map between charging schemes 2 (FIG. 4D) and 1 (FIG. 4C), it is worth noting that the field strength represented by the contour map for these two instances have also changed (not shown).

FIGS. 4A-4D are simple 2D models mainly to represent the idea that different charging schemes (and embodiments) can allow the electric-field enhancement to be (actively) fine tuned in a device or general catalysis process. The field distribution, etc. may be different in a real device or process because the presence of the sensing electrodes and other components will also contribute to the field, making it different from the simple cases shown. The electrostatic and chemical interaction with the device, catalyst, gas, adsorbates, etc. will depend on these field contour and vector maps. Therefore, these interactions can be (actively) fine tuned depending on the device or general catalysis process for a given application.

Figure 5A:
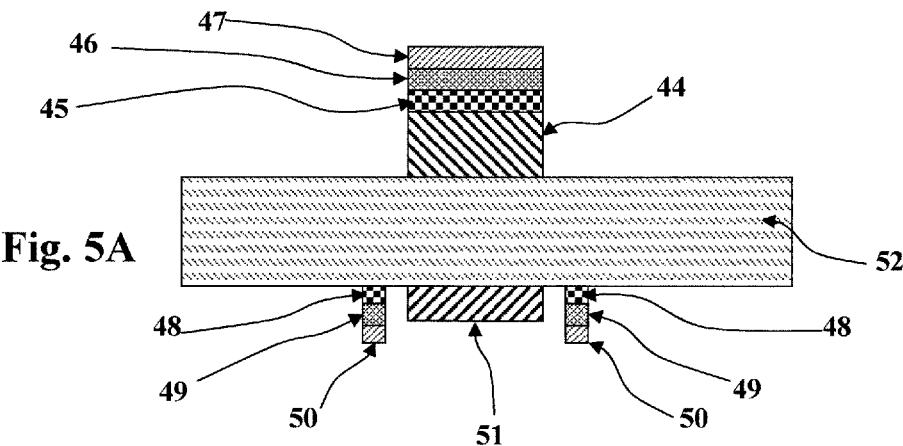
FIGS. 5A-5C show a planar gas sensor according to an embodiment of the present invention.

FIG. 5A represents a sensor embodiment utilizing an air-reference electrode 51. This embodiment was used to show that catalytic reactions are changing during use of the electric field electrodes, as exhibited by alteration of the measured gas composition. Insulation layers 45 and 48, conduction layers 46 and 49, and cap layers 47 and 50 making up four "electric-field electrodes." Sensing electrode 44 and air-reference electrode 51 are attached to substrate (electrolyte or other material) 52.

Figure 5B:
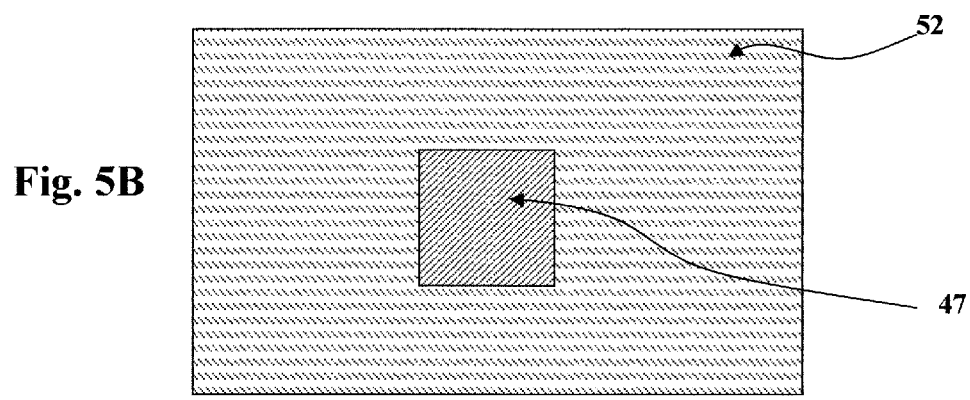

FIG. 5B shows a top surface of the air-reference sample with "electric-field electrodes" embodiment, with cap layer 47 shown. Metallic leads or other metallization (not shown) can be attached to the sensing or air-reference electrodes in many ways. For the sensor application these leads are used to transmit information about the EMF at the electrode to a measurement device. Multiple sensing electrodes and "electric-field electrodes" may be incorporated into such a device as well, making it a gas sensor array.

Figure 5C:
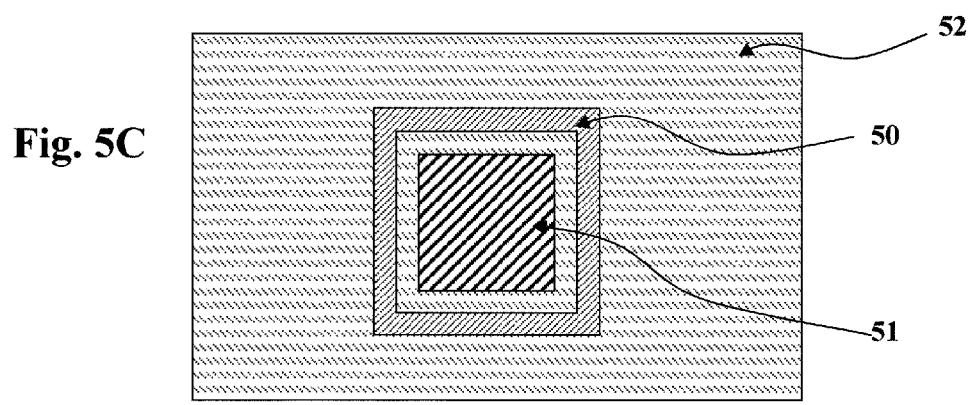

FIG. 5C shows a bottom surface of the air-reference sample with "electric-field electrodes" embodiment. Air-reference electrode 51 is attached to substrate 52, and surrounded by the "electric-field electrode on this surface. From this viewpoint, the cap layer 50 is visible.

This sensor device includes a first, rectangular ring-shaped "electric-field electrode" on one side of an electrolyte. In the middle this rings, a Pt air-reference electrode was deposited. On the opposite side, a $La_2CuO_4$ electrode was attached to the electrolyte. On top of this electrode was a second, plate-shaped "electric-field electrode". The La2CuO4 electrode and second field electrode were exposed to the active gas stream, while the Pt air-reference and first field electrode remained at constant oxygen partial pressure (i.e., air).

Figure 6A:
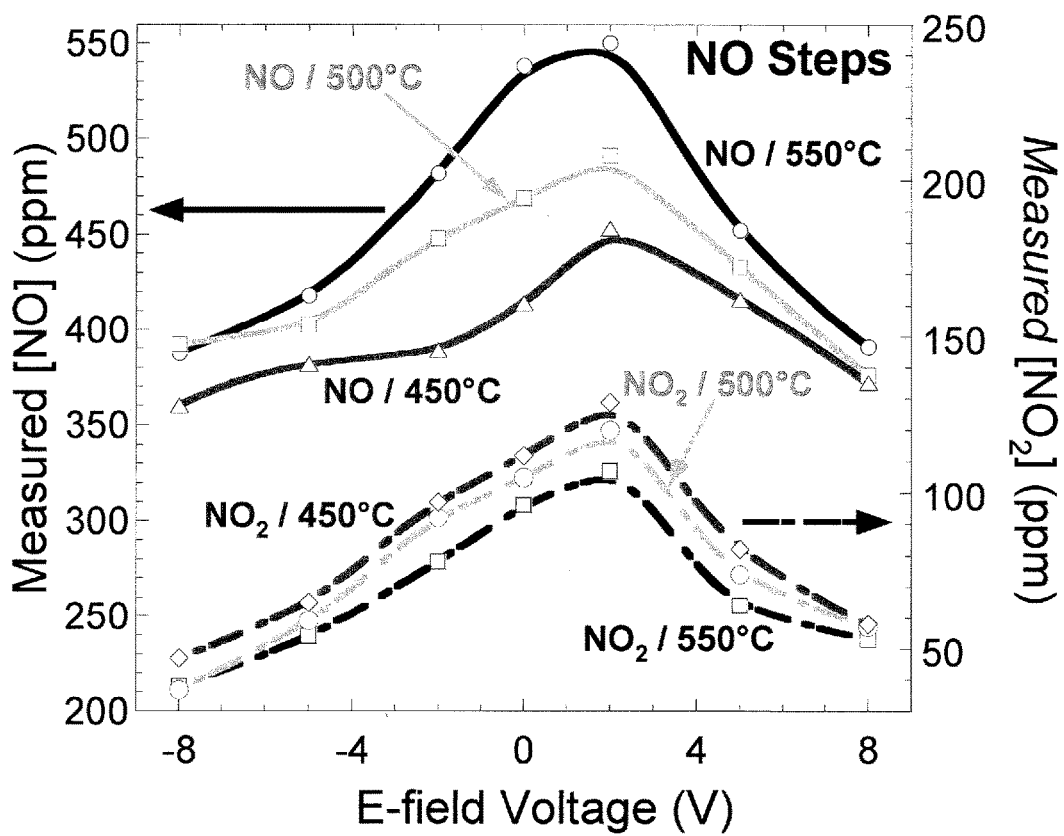
FIGS. 6A-6B show mass spectrometry comparisons of the changes in $NO_x$ concentrations coming off the semiconducting material for various applied field voltages during exposure to gas feed compositions of 650 ppm NO or $NO_2$ at various temperatures, according to the embodiment shown in FIGS. 5A-5C.
Figure 6B:
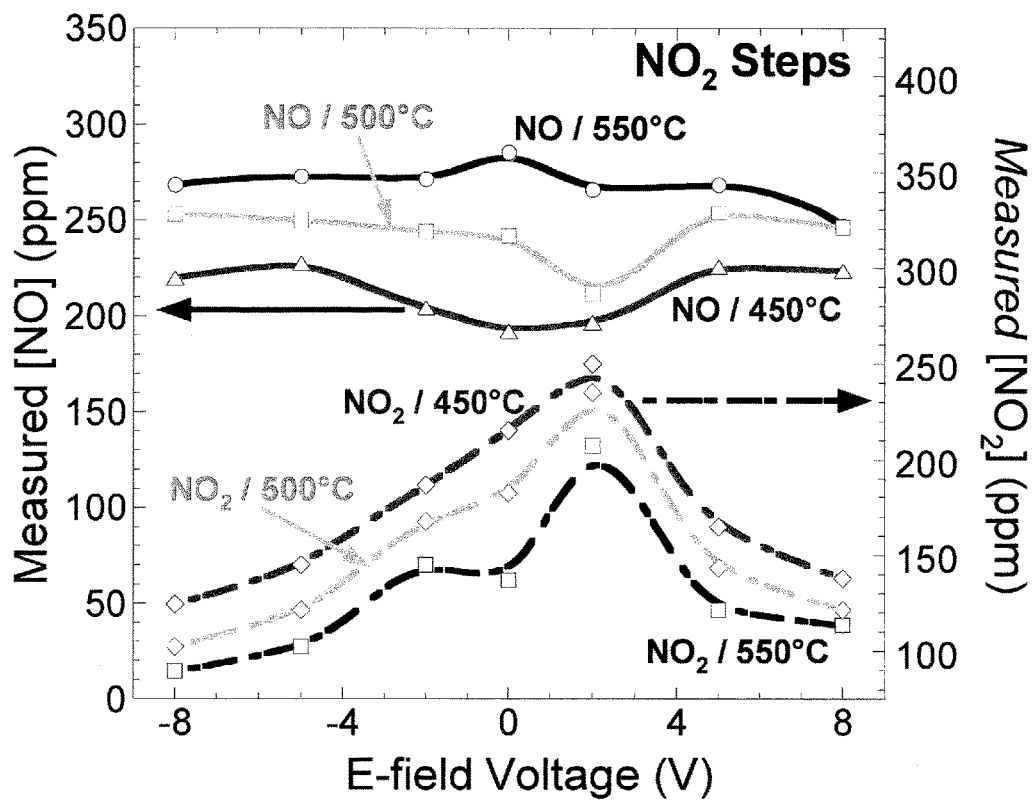

The sensor was evaluated for multiple NOx concentrations in 3% O2 under an "electric-field electrode" bias of 0, 2, 5, and 8 V in the positive (high potential on La2CuO4 side) and negative (high potential on Pt side) directions. These tests were performed at temperatures of 450° C., 500° C., and 550° C. and repeated twice for each condition. The sensors under the influence of the electric field were compared to the unbiased device at each temperature. The sensor signals were very low at 550 C and 500 C, which resulted in little or no change in sensitivity with applied field (not shown), except for the −8 V setpoint with NO at 500 C. However, as seen in FIGS. 6A and 6B, at all temperatures, alteration of the field bias produced changes in the gas composition coming off the La2CuO4 sensing electrode as detected with mass spectrometry. These plots were made using the measured NOx compositions from the 650 ppm NO or NO2 feed composition of the respective gas steps. These plots are in terms of electric-field bias voltage because of the difficulty in ensuring the modeled field-strengths accurately represent reality when applied to handmade samples. As evident from both plots in FIG. 4, there were major changes in NOx levels for both NO and NO2 gas steps. Furthermore, in the case of the NO2 gas steps, a shoulder/peak evolves in the measured NO2 curves (around −5 V field bias) as temperature increases.

Figure 6C:
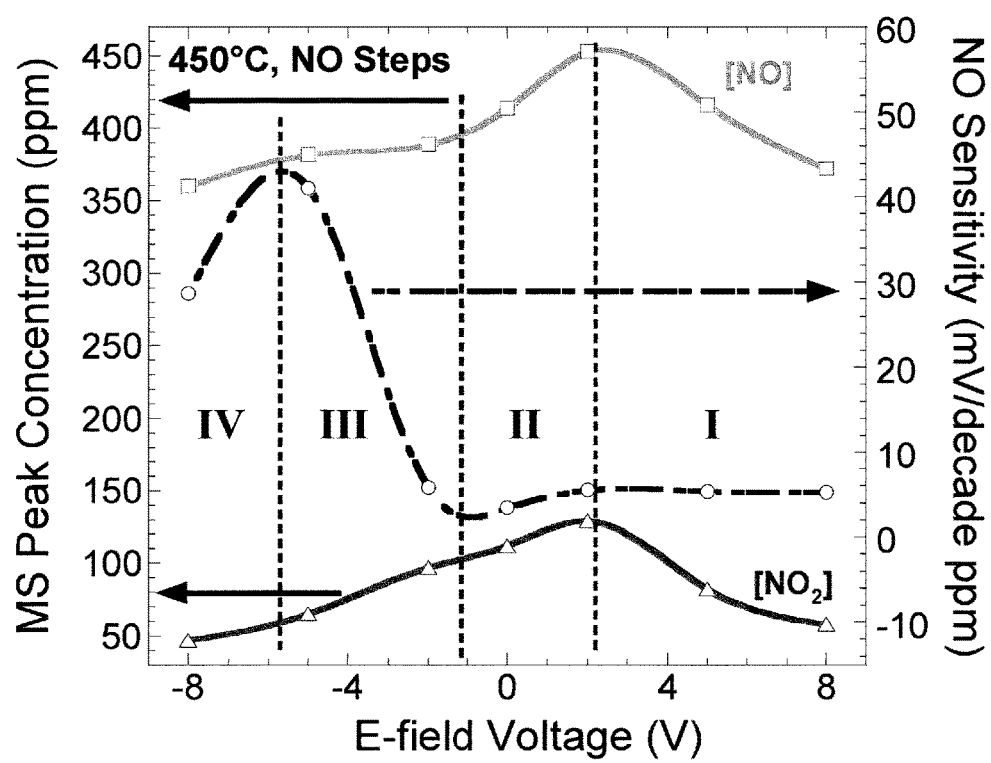
FIGS. 6C-6D show sensitivity plots of the planar gas sensor according to the embodiment in FIGS. 5A-5C to NO and $NO_2$ and the corresponding changes in $NO_x$ concentrations during the 650 ppm feed composition, all at 450 C.
Figure 6D:
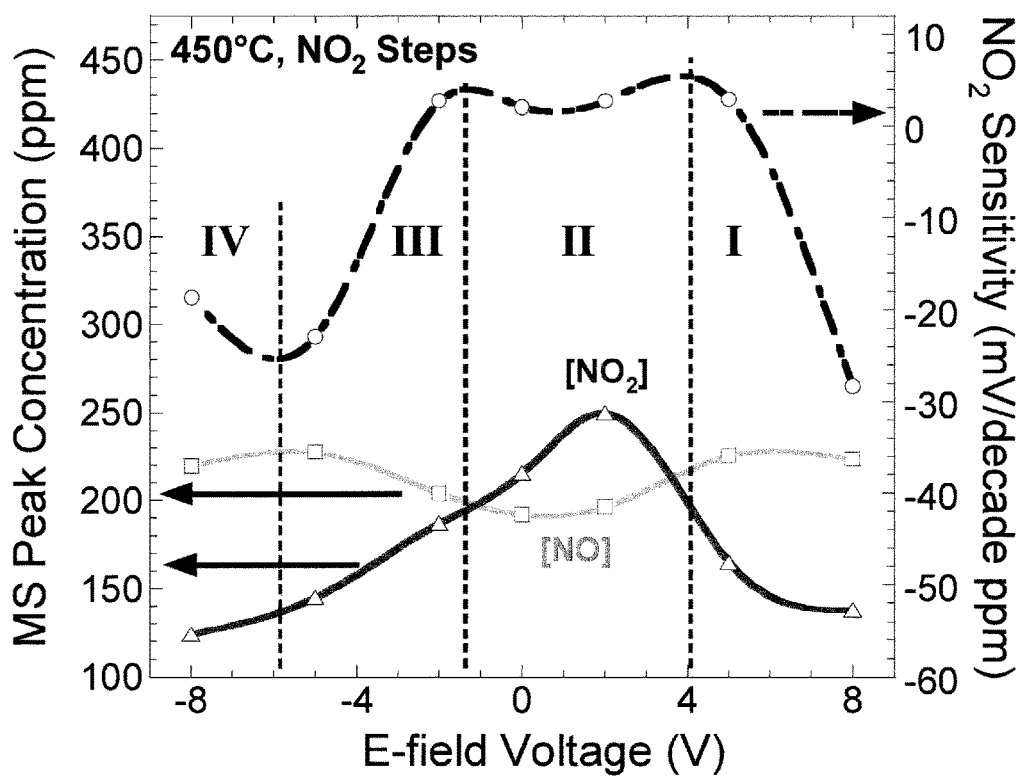

At 450° C., there were significant changes for both NO and NO2 sensitivity as the electric field was created on the device. The sensitivity (mV/decade ppm NOx) to gas steps and concentrations measured during the 650 ppm NO or NO2 feed composition can be seen in FIGS. 6C and 6D. In the case of NO gas steps, from region I to II a decreasing (+) field bias resulted in concurrent increases of NO and NO2 concentrations without much change in sensitivity. In region II, a transition from (+) to (−) field bias occurred with the result of a sharp decrease in measured NO and a more gradual decrease in NO2. This difference in the change of species concentrations appears to have caused the sensitivity to decrease in going from region II to III. With a further decrease in the now (−) field bias there resulted a continuing decrease in NO2 levels with essentially no change in NO. This was accompanied with a dramatic increase in the NO sensitivity of the device. Finally in transition from region III to IV, there was a relatively large decrease in sensitivity as the NO and NO2 concentrations dropped in response to a more (−) field bias.

Now considering the four regions of inflection in FIG. 5 for NO2 gas steps at 450° C., there appear to have been more complicated changes to the sensing mechanism. In going from region I to II, there was a sharp increase in the NO2 concentration accompanied with a slower decrease in NO. This resulted in a sharp shift in the NO2 sensitivity to smaller, more positive values. In the middle of region II, there was a crossover of the NO and NO2 concentrations with a concomitant dip in NO2 sensitivity. After a small increase at the more (−) end of region II, there was a sharp decrease in NO2 sensitivity as region III begins. Also during this transition was a second crossover of the NO and NO2 concentrations as the amount of NO2 decreased sharply and NO more slowly increased. As region III nears region IV, the measured NO concentration began to inflect and decreased while the NO2 continued to decrease. As a result, the NO2 sensitivity increased slightly in region IV.

The results from the embodiment in FIGS. 5A-5C, as shown in FIGS. 6A-6D demonstrate that use of the electric field electrodes can change the catalytic properties of a material, which may be used in an electrochemical device, non-electrochemical device, or other related (catalytic) processes. Furthermore, these results can enhance a gas sensor by causing large changes in sensitivity to various gas species.

Figure 7A:
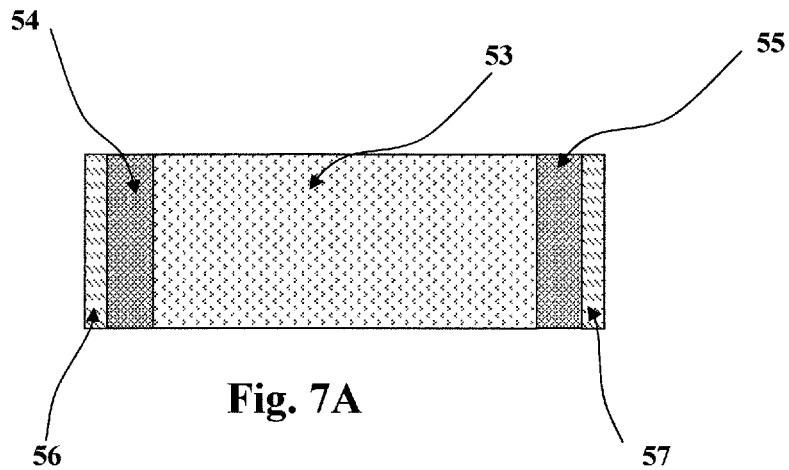
FIG. 7A shows schematic of a sample used for temperature programmed desorption (TPD) tests.
Figure 7B:
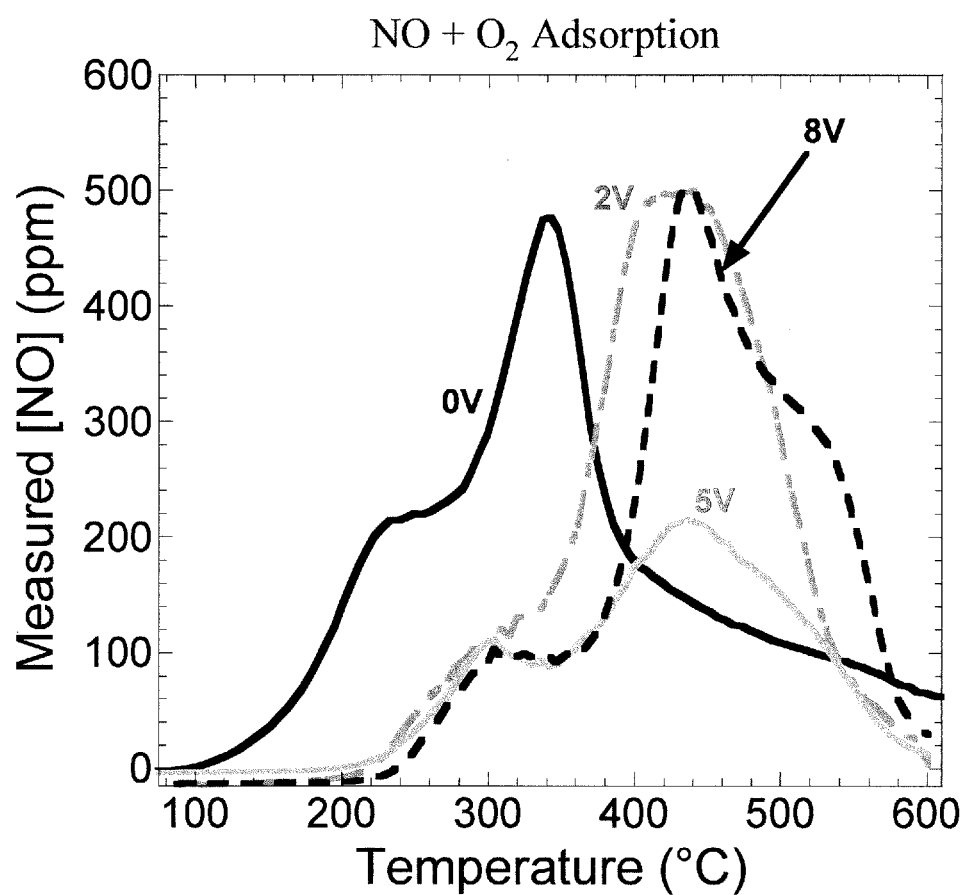
FIGS. 7B-7E show plots of desorption profiles.
Figure 7C:
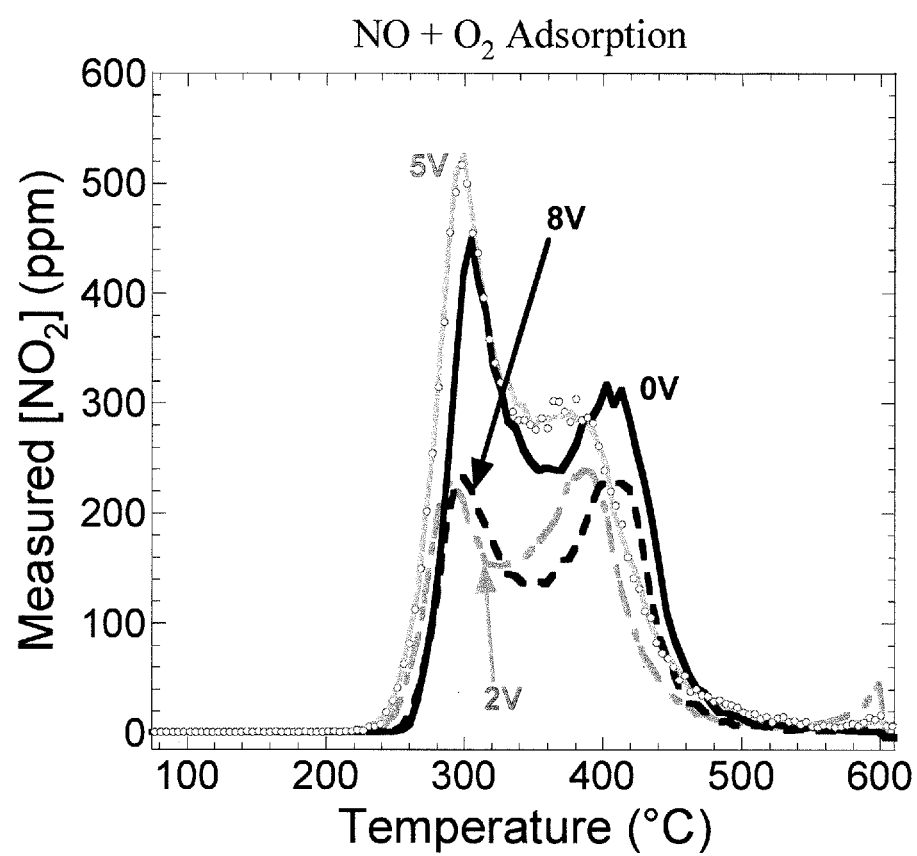

The sample shown in FIG. 7A was used in the field-assisted desorption measurements shown in FIG. 7B through 7E. These results demonstrated that an indirectly applied electric field can affect the behavior of NOx on the surface of $La_2CuO_4$ even at relatively small field strengths. Temperature Programmed Desorption (TPD) experiments were conducted on a sample with "electric-field electrodes" as shown in FIG. 7A. This sample included a section of a porous $La_2CuO_4$ bar 53 with insulating layer 54 and 55 ($Al_2O_3$) and conducting layers 56 and 57 an (Au) attached to either end. Though not shown, an effect was also seen on a high-surface area powder sample of $La_2CuO_4$. During several sets of experiments, the sample was biased at the conduction layers 56 and 57 with various applied voltages.

TPD is an experimental technique in which initial quantities of a gas are adsorbed at relatively low temperatures (e.g., 300 C) and then cooled to room temperature. The gas of interest is then shut off, and an inert gas such as helium is flowed through the reactor. The temperature is then ramped at high linear rate (e.g., 30° C./min) as the evolution of desorbed species is monitored with a mass spectrometer.

As the electric-field voltage setpoint increased, the desorption peaks for NO (FIG. 7B) shifted to higher temperatures, while maintaining similar initial peak shapes, albeit different intensities. In addition to the upward temperature shift of the peaks, the lingering desorption of NO at high temperatures was expressed as more defined peaks. This shift was accompanied by the appearance of substantial $NO_2$ desorption peaks at the same temperatures as NO desorption (FIG. 7C. Changes in peak intensity and area indicate that the adsorption/desorption energies and chemisorption mechanisms are likely changing as a result of the electric-field. The quantity of gases desorbed from the sample can be found in Table 3.

TABLE 3

NO Adsorption
TABLE 3. Total amount $NO_x$ adsorbed during $NO + O_2$ TPD.

| E-field Bias Voltage | Total μmol NO Adsorbed | Total μmol $NO_2$ Adsorbed | Total μmol $NO_x$ Adsorbed |
|---|---|---|---|
| 0 V | 13.080 | 7.848 | 20.868 |
| 2 V | 13.450 | 5.165 | 18.615 |
| 5 V | 6.706 | 8.591 | 15.297 |
| 8 V | 11.040 | 4.994 | 16.034 |

Figure 7D:
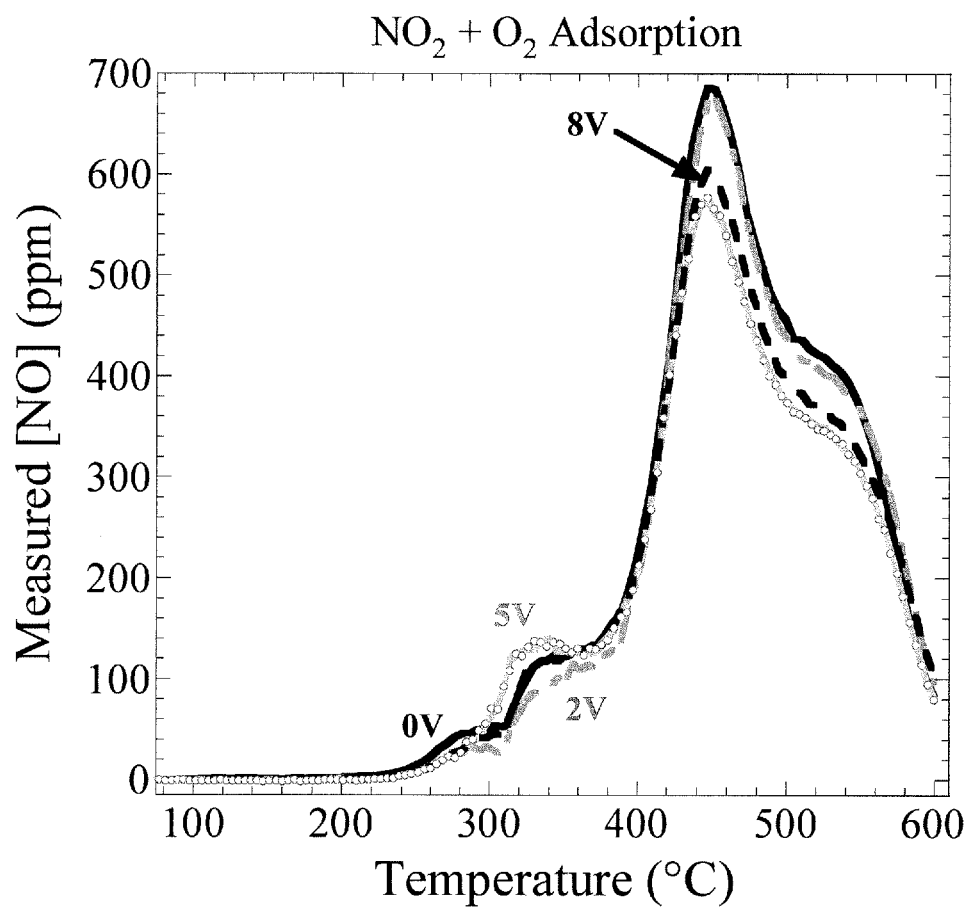
Figure 7E:
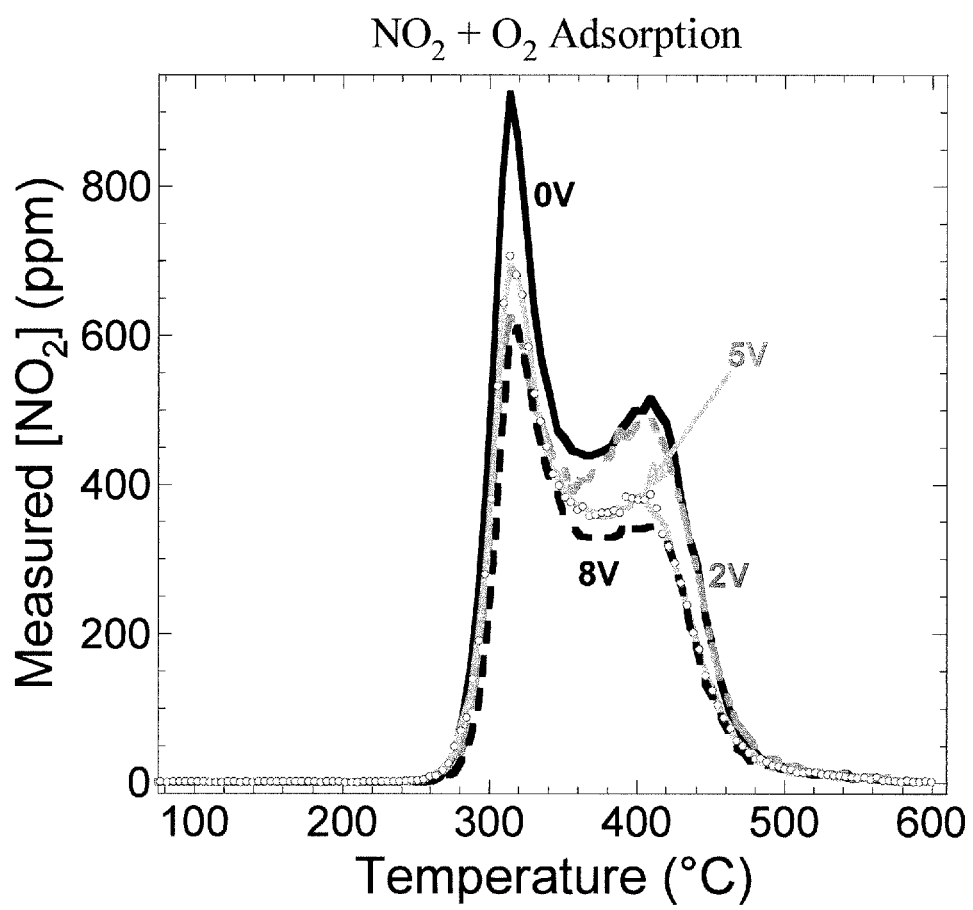

Identical experiments were performed for NO2 adsorption (FIGS. 7D and 7E). In these results, there were less pronounced shifts in the desorption energies, but definitive changes in the intensities of the various peaks indicates possible changes in chemisorption mechanisms. Desorption amounts can be seen in Table 4.

TABLE 4

$NO_2$ Adsorption
TABLE 4. Total amount $NO_x$ adsorbed during $NO_2 + O_2$ TPD.

| E-field Bias Voltage | Total μmol NO Adsorbed | Total μmol $NO_2$ Adsorbed | Total μmol $NO_x$ Adsorbed |
|---|---|---|---|
| 0 V | 15.220 | 13.240 | 28.460 |
| 2 V | 14.550 | 11.470 | 26.020 |
| 5 V | 13.290 | 10.380 | 23.670 |
| 8 V | 14.000 | 9.105 | 23.105 |

Sensor embodiments in accordance with the subject invention can utilize potentiometric, impedancemetric, and/or amperometric measurements. The sensors can locate all of the electrodes in the same gas environment and can use an air reference or some other type of reference.

In various embodiments, the voltage(s) applied to the "electric-field electrodes" may be alternatively supplied with a potentiostat or other device that keeps the charge at the "electric-field electrodes" equal to the desired value. In this way if the gas environment (or some phenomena) causes the charge to change, the potentiostat or other device can counteract to ensure the charge returns to the desired value. The charge may be calculated from a measured current change with time as, at least in the ideal case, there is no electronic current flowing through the device as a result of the applied voltage to the "electric-field electrodes". This current measured in the "circuit" occurs as a result of changes in the accumulated charge at the insulating layer, which is only a perfect insulator in the ideal case.

Figure 8A:
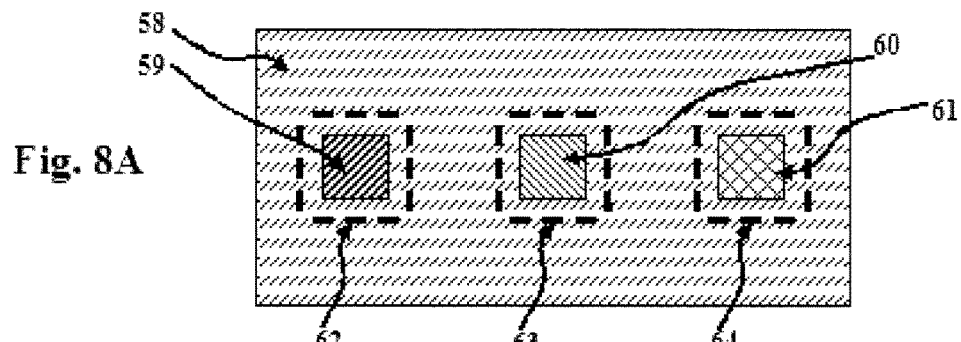
Figure 8B:
Figure 8C:
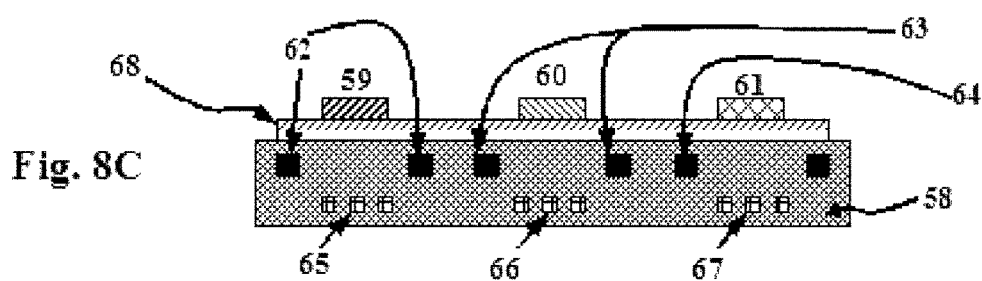

FIGS. 8A-8H represent some of the other various configurations in which the electric-field enhancements may be used. FIG. 8A shows a top view of a substrate 58 (electrolyte or other material), with each sensing electrode 59, 60, and 61 surrounded by several "electric-field electrodes" 62, 63, and 64 forming a dashed ring shape around the sensing electrodes. In FIGS. 8A-8H, the electric-field electrodes are shown as one body, consisting of at least an insulating layer and conducting layer and possibly a cap layer as was shown in the embodiment of FIG. 2A-2C. FIG. 8B shows the cross-section of FIG. 8A, with the sensing electrodes 59, 60, and 61 and "electric-field electrodes" 62, 63, and 64 displayed on one surface and heater structures 65, 66, and 67 (serpentine or other pattern) on a second surface. FIG. 8C shows the cross-section of 8A, but now with the "electric field electrodes" 62, 63, and 64 and heater structures 65, 66, and 67 embedded within the substrate 58. Furthermore, there is a new layer 68 (electrolyte or other material) between the substrate 58 and sensing electrodes 59, 60, and 61.

Figure 8D:
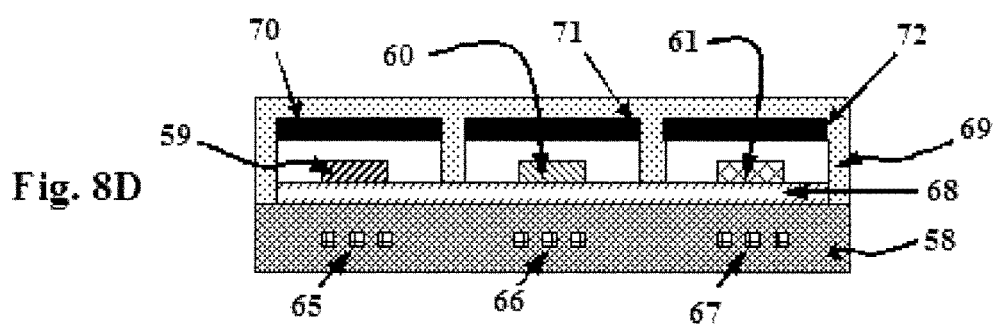
Figure 8E:
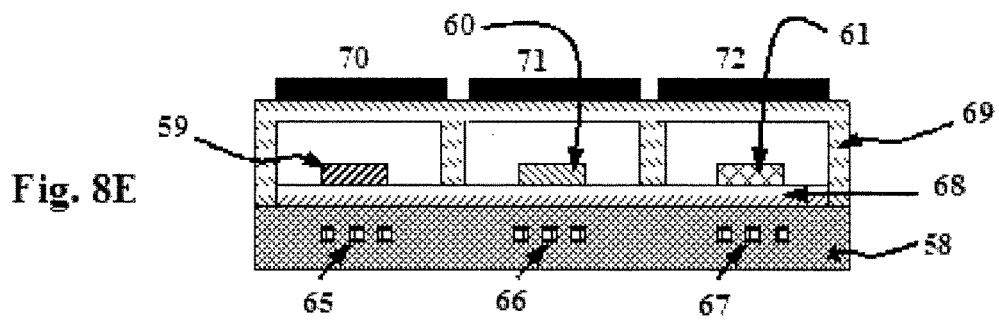

FIGS. 8D and 8E show cross-sections of FIG. 8A, with heater structures 65, 66, and 67 embedded in the substrate and second layer 68 between substrate 58 and sensing electrodes 59, 60, and 61; the electric-field electrodes 70, 71, and 72 now have the form of plate-like shapes rather than the dashed arrangement seen in FIG. 8A. Furthermore, FIG. 8D shows a structure 69 that creates a cavity above each sensing electrode 59, 60, and 61; the electric field electrodes 70, 71, and 72 are attached to the inner side of this structure. FIG. 8E shows a similar cavity creating structure 69, but with the electric field electrodes 70, 71, and 72 on the top surface of this structure.

FIGS. 8F-8H show several additional configurations of devices utilizing the electric-field enhancements. FIG. 8F shows the top view of the embodiment with two rectangular layers 83 and 84 (electrolyte or other material) on top of the substrate 76 (electrolyte or other material) containing at least two sensing electrodes 79, 80, 81, and 82 each. Layers 83 and 84 serve to separate the sensing electrodes 79, 80, 81, and 82 from the substrate 76. Structures 72 and 78 surround each of these rectangular layers and represent several electric field electrodes in a dashed arrangement. FIG. 8G represents a cross-section of FIG. 8F, showing rectangular layers 83 and 84 and corresponding sensing electrodes 79, 80, 81, and 82. Also shown are electric-field electrodes 77 and 78, and heating structures 68 and 70 on the bottom surface. FIG. 8H shows another possible embodiment where one of the rectangular layers (83 in 8F) with sensing electrodes (79 and 80 in 8F) are replaced with a gas sensitive material 85 (e.g., electrical resistance changes upon gas exposure) in contact with the substrate 76. Electrical contacts 86 and 87 are made to this material in two places. The remainder of this embodiment is the same as in 8G.

In a fuel cell (e.g., SOFC) oxygen is dissociation on the cathode and fuel dissociation and reactions at the anode. As discussed herein, the presence of an electric field can stabilize/destabilize adsorbate complexes on a surface. This may result in alterations to the kinetics or reaction mechanisms that will improve the performance of a fuel cell (e.g., enhance power density output). Furthermore, as discussed, removal or prevention of the buildup of poisons from the fuel cell surface, particularly at the fuel side can be accomplished in accordance with embodiments of the invention using "electric-field electrodes". The use of "electric-field electrodes" with SOFC can lower the operating temperatures and allow the use of cheaper materials in the fuel cells. Furthermore, the electric-electrodes may be used to modify the device for enhanced or maintained performance when load conditions change.

Figure 9A:
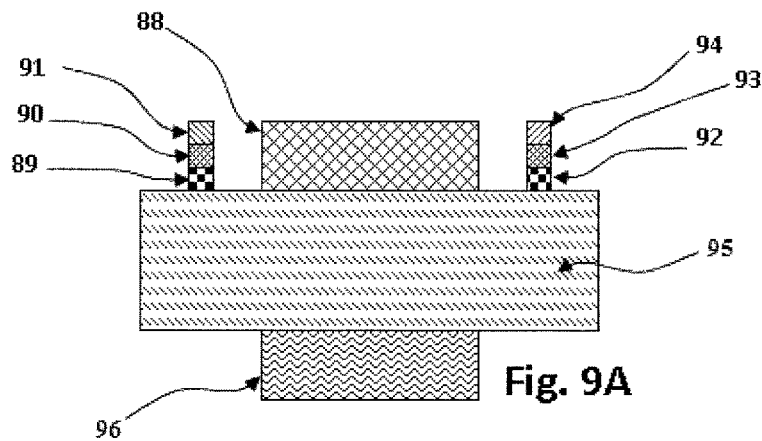
FIGS. 9A-9C show an electrochemical device (e.g., a fuel cell) according to an embodiment of the present invention.

FIG. 9A represents an electric-field enhanced, electrochemical cell (e.g., fuel cell) embodiment. Here, substrate 95, which may be an electrolyte, has an attached anode (88 or 96) and cathode (96 or 88). In other embodiments, other materials serve as the support or other support material, such as an anode support, with the electrolyte and other corresponding layers on top. Different arrangements can be used where the device is anode supported, and the electrolyte is a very thin layer attached to the support. The cathode can then be deposited on top of the electrolyte, completing the cell. The "electric-field electrodes" are made up of insulation layers 89 and 92, conduction layers 90 and 93, and cap layers 91 and 99. Metallic leads, or other interconnections (not shown), may be attached to the electrodes in many different ways. This arrangement also may be formed into a stack made up of multiple cells.

Figure 9B:
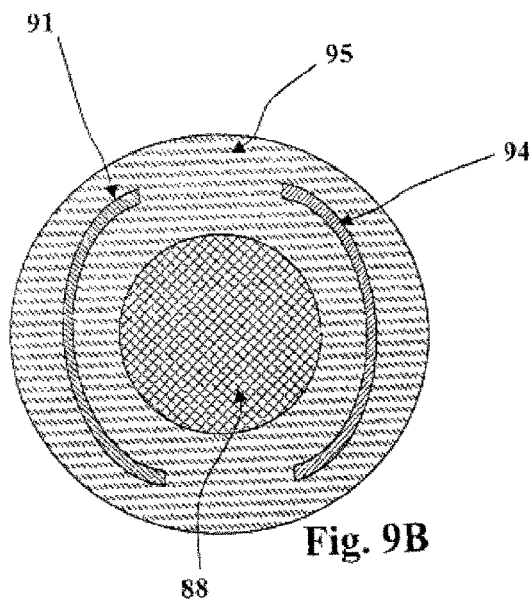
Figure 9C:
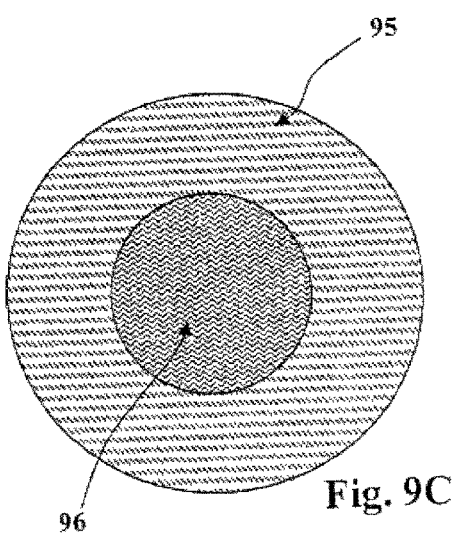

FIG. 9B is one surface of the electrochemical cell (e.g., fuel cell) embodiment. Here, cap layers 91 and 94 are visible. Electrode 88 may be the anode or cathode and is attached to substrate 95. FIG. 9C is another surface of the fuel cell embodiment. Here only electrode 96 is visible. It is attached to substrate 95 and may be the anode or cathode.

Figure 10A:
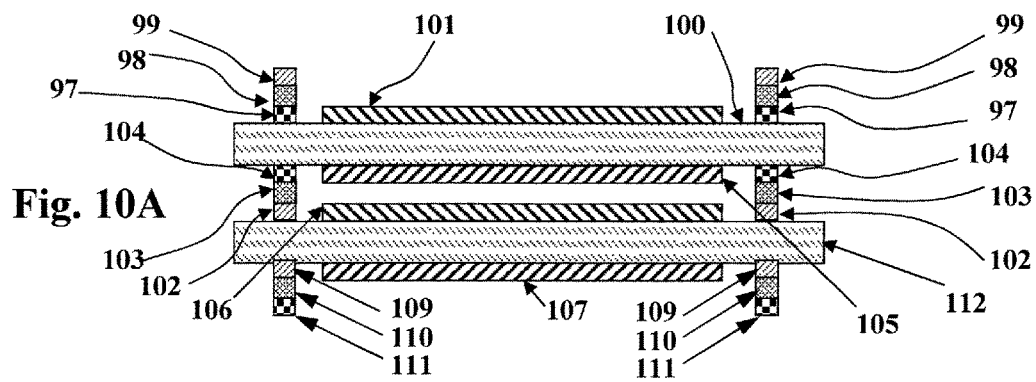
FIGS. 10A-10C show an electrochemical device (e.g., a fuel cell) according to an embodiment of the present invention.
Figure 10B:
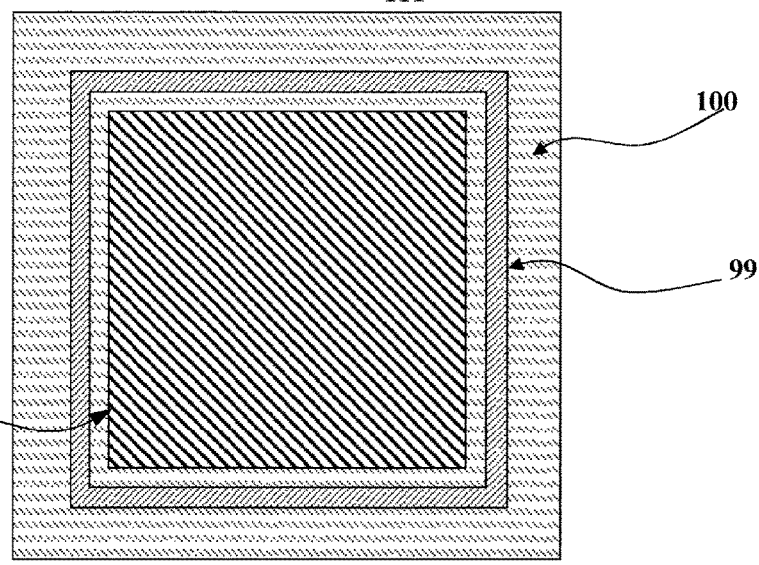
Figure 10C:
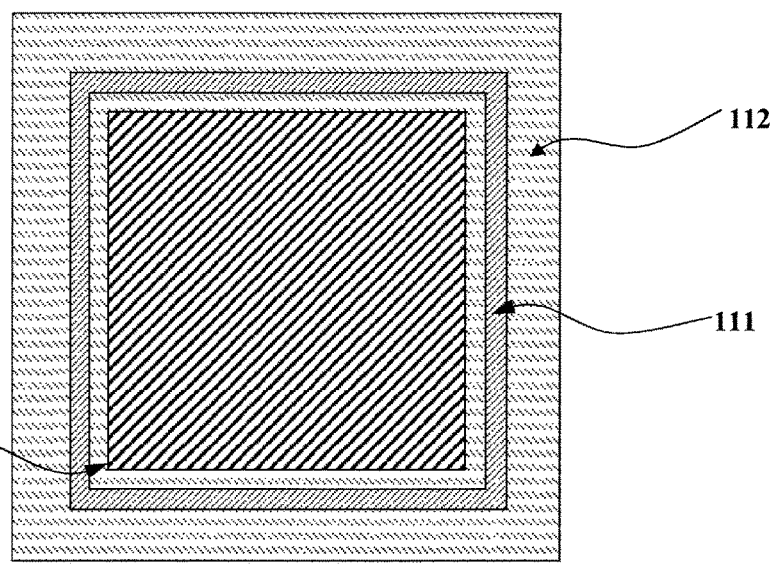

FIGS. 10A-10C show a different electric-field enhanced, electrochemical device (e.g., fuel cell) embodiment in a planar configuration. Shown is a stack configuration which may consist of any number of cells. In FIG. 10A, several electric field electrodes exist, consisting of conducting layers 98, 103, and 110 insulating layers 97, 99, 102, 104, 109, and 111. In this configuration, the distinction between insulating layers and cap layers is insignificant. These layers are deposited on substrates 100 and 112, which have various electrodes 101, 105, 106, and 107 (anodes and cathodes) attached. Though not necessary, in some cases the electric field electrodes have the added benefit of acting as seals to separate gases between the various electrochemical cells. FIG. 10B shows the top surface of the embodiment in FIG. 10A with substrate 100, electrode 101 (anode or cathode), and insulating layer 99 of an electric field electrode. FIG. 10C shows the bottom surface of the embodiment in FIG. 10A with substrate 112, electrode 107 (anode or cathode), and insulating layer 111 of an electric field electrode.

NEMCA can greatly enhance catalytic reaction rates. In the case of NEMCA, the electric field created by the applied potential or (electronic) current to the cell electrodes is limited due to the fact that increased potential (and thus field strengths) can result in permanent damage of the device. However, use of the "electric-field electrodes" can enhance the NEMCA electric field. Furthermore, the "electric-field electrodes" can have more control over adsorption and reactions than NEMCA because they may be located anywhere on the device.

As discussed herein, catalytic reactions may be altered with the use of electric fields. The "electric-field electrodes" may be incorporated into a catalyst support and thereby alter reaction pathways in a desirable way. Improvements include increased conversion yield and/or lower temperature requirements for reactions. This can result in lower costs and improved profitability for catalytic reactions.

Figure 11A:
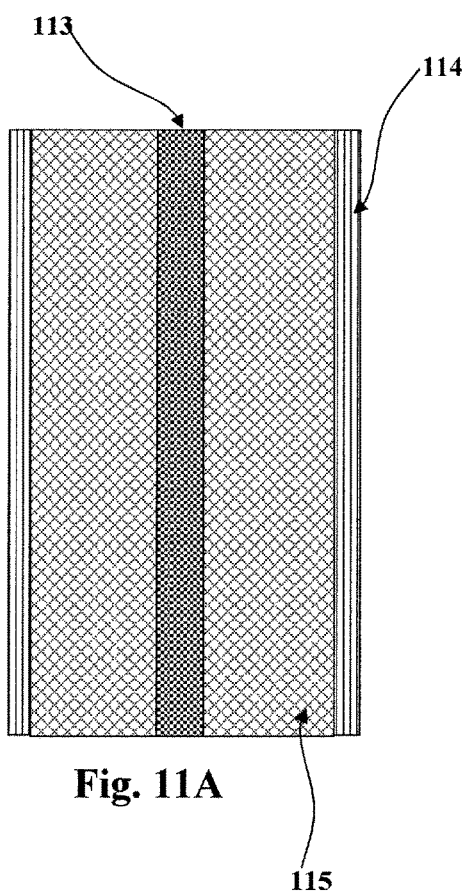
FIGS. 11A-11C show a catalyst bed according to an embodiment of the present invention.

FIG. 11A represents a cross-section of catalyst bed embodiment used in catalysis processes. Metal core 113 is embedded through the middle of honeycomb 115. Outer electrode 114 is attached to the perimeter of honeycomb 114. The honeycomb pattern also may be another related shape, whose purpose is to hold catalyst particles 116. This embodiment is a polygonal-cylinder, and a voltage is applied between metal core 113 and outer electrode 114 to create an electric field around the catalyst particles which are dispersed throughout the honeycomb 115 structure. The reactant gas is flowed through the honeycomb 115 structure, where it can react on the catalyst particles. Note that the honeycomb 115 structure can also be made from an electrolyte material. In this case, an insulation layer is placed between the metal core 113 and the honeycomb 115. An insulation layer is also placed between the outer electrode 114 and the honeycomb 115 structure. Furthermore, an embodiment such as this with an electrolyte honeycomb 115 structure can be operated in an electric-field enhanced mode.

Figure 11B:
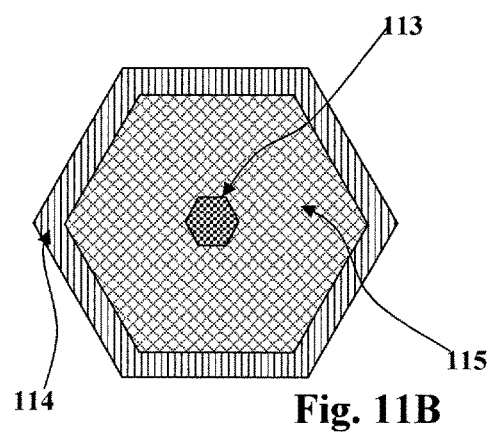
Figure 11C:
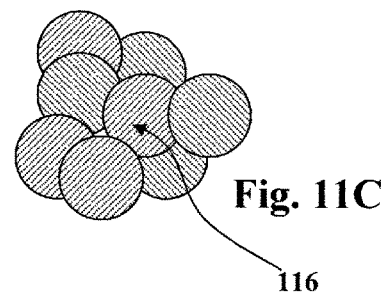

FIG. 11B represents a top view of the polygonal-cylinder shape, with metal core 113 and outer electrode 114 shown. The honeycomb 115 structure is also shown. FIG. 11C represents a cluster of catalyst particles 116 that could be dispersed throughout the honeycomb structure seen in FIGS. 11A and 11B.

In all embodiments shown and any others utilizing the electric field electrodes, when an electrochemical cell is involved, a combined NEMCA effect (direct bias) and electric-field enhancements (provided by the "electric-field electrodes") can improve the catalysis as discussed elsewhere. Also, multiple "electric-field electrodes" may be used in such configurations or related embodiment.

EMBODIMENTS

Embodiment 1

An electrochemical cell, comprising:
a substrate, wherein the substrate comprises an electrolyte;
at least two sensing electrodes, wherein the at least two sensing electrodes are positioned on the substrate, wherein the at least two sensing electrodes are in electrical contact with the electrolyte;
a means for creating an electric field proximate at least one of the at least two sensing electrodes;
a means for measuring a characteristic with respect to one or more of the at least two sensing electrodes, wherein creating the electric field proximate the at least two sensing electrodes alters the measured characteristic.

Embodiment 2

The electrochemical cell according to Embodiment 1, wherein the characteristic is an electrical characteristic.

Embodiment 3

The electrochemical cell according to Embodiment 1, wherein the characteristic is temperature.

Embodiment 4

The electrochemical cell according to Embodiment 2, wherein the electrical characteristic is a voltage between two of the at least two sensing electrodes.

Embodiment 5

The electrochemical cell according to Embodiment 2, wherein the electrical characteristic is a current flowing between two of the at least two sensing electrodes.

Embodiment 6

The electrochemical cell according to Embodiment 2, wherein the electrical characteristic is an impedance between two of the at least two sensing electrodes.

Embodiment 7

The electrochemical cell according to Embodiment 2, wherein the electrical characteristic is an resistance between two of the at least two sensing electrodes.

Embodiment 8

The electrochemical cell according to Embodiment 2, wherein the electrical characteristic is an capacitance between two of the at least two sensing electrodes.

Embodiment 9

The electrochemical cell according to Embodiment 2, further comprising:
a means for modifying a temperature of at least one of the at least two sensing electrodes, wherein modifying the temperature alters the measured electrical characteristic.

Embodiment 10

The electrochemical cell according to Embodiment 9, further comprising:
a means for monitoring the temperature of the at least one of the at least two sensing electrodes.

Embodiment 11

The electrochemical cell according to Embodiment 1, wherein the electrochemical cell is a gas sensor.

Embodiment 12

The electrochemical cell according to Embodiment 1, wherein the means for creating the electric field is positioned on the substrate.

Embodiment 13

The electrochemical cell according to Embodiment 12, wherein the means for creating the electric field comprises at least one electric field electrode positioned on the substrate.

Embodiment 14

The electrochemical cell according to Embodiment 13, wherein the at least one sensing electrode and the at least one electric field electrode are positioned on opposite sides of the substrate.

Embodiment 15

The electrochemical cell according to Embodiment 13, wherein the at least one sensing electrode and the at least one electric field electrode are positioned on the same side of the substrate.

Embodiment 16

The electrochemical cell according to Embodiment 13, wherein each of the at least one electric field electrodes comprises a conducting layer and an insulation layer, wherein the insulation layer is positioned between the substrate and the conducting layer.

Embodiment 17

The electrochemical cell according to Embodiment 2, wherein the means for measuring the electrical characteristic with respect to one or more of the at least two sensing electrodes measures a time dependence of the electrical characteristic of the one or more of the at least two sensing electrodes.

Embodiment 18

The electrochemical cell according to Embodiment 11, wherein the gas sensor measures a concentration of a component of a gas mixture.

Embodiment 19

The electrochemical cell according to Embodiment 11, wherein the gas sensor detects a presence of a gas.

Embodiment 20

The electrochemical cell according to Embodiment 18, wherein a first of the at least two sensing electrodes is positioned on a first surface of the electrolyte, wherein a second of the at least two sensing electrodes is positioned on the first surface of the electrolyte, wherein the means for measuring a characteristic with respect to one or more of the at least two sensing electrodes comprises a means for measuring a voltage between the first sensing electrode and the second sensing electrode.

Embodiment 21

The electrochemical cell according to Embodiment 20, wherein the means for creating an electric field proximate at least one of the at least two sensing electrodes creates the electric field proximate the first sensing electrode.

Embodiment 22

The electrochemical cell according to Embodiment 21, wherein the means for creating the electric field creates the electric field proximate the second sensing electrode.

Embodiment 23

The electrochemical cell according to Embodiment 21, wherein the means for creating the electric field comprises at least one electric field electrode.

Embodiment 24

The electrochemical cell according to Embodiment 23, wherein the at least one electric field electrode comprises a first ring-shaped electrode surrounding the first sensing electrode.

Embodiment 25

The electrochemical cell according to Embodiment 1, further comprising a reference electrode positioned on the substrate.

Embodiment 26

The electrochemical cell according to Embodiment 18, wherein the component is NO.

Embodiment 27

The electrochemical cell according to Embodiment 18, wherein the component is $NO_2$.

Embodiment 28

The electrochemical cell according to Embodiment 18, wherein the component is selected from the following group: ammonia, $SO_2$, $SO_3$, hydrocarbons, $H_2$, $H_2O$, CO, and $CO_2$.

Embodiment 29

The electrochemical cell according to Embodiment 18, further comprising a means for determining the concentration of the component from the measured electrical characteristic.

Embodiment 30

The electrochemical cell according to Embodiment 1, wherein the means for creating the electric field is not in electrical contact with the substrate.

Embodiment 31

A device, comprising:
a substrate;
at least one sensing electrode, wherein the at least one sensing electrode is positioned on the substrate;
a means for creating an electric field proximate one of the at least one sensing electrode;
a means for measuring a characteristic with respect to one of the at least one sensing electrode.

Embodiment 32

The device according to Embodiment 31, wherein the characteristic is an electrical characteristic.

Embodiment 33

The device according to Embodiment 32, wherein the electrical characteristic is an impedance of the one of the at least one sensing electrodes

Embodiment 34

The device according to Embodiment 32, wherein the electrical characteristic is a resistance of the one of at least one sensing electrode.

Embodiment 35

The device according to Embodiment 32, wherein the electrical characteristic is a capacitance of the one of at least one sensing electrode.

Embodiment 36

The device according to Embodiment 32, wherein the means for measuring an electrical characteristic measures a time dependence of the electrical characteristic of the one of the at least one sensing electrodes.

Embodiment 37

The device according to Embodiment 32, wherein the substrate comprises an electrolyte, wherein the one of the at least one sensing electrode is in electrical contact with the electrolyte.

Embodiment 38

The device according to Embodiment 32, wherein the electrical characteristic is an impedance between two of the at least one sensing electrode.

Embodiment 39

The device according to Embodiment 31, wherein the characteristic is temperature.

Embodiment 40

The device according to Embodiment 32, further comprising:
a means for modifying a temperature of at least one of the at least one sensing electrode, wherein modifying the temperature alters the measured electrical characteristic.

Embodiment 41

The device according to Embodiment 40, further comprising:
a means for monitoring the temperature of the at least one of the at least one sensing electrode.

Embodiment 42

A catalysis device, comprising:
a substrate, wherein the substrate comprises an electrolyte;
at least two electrodes, wherein the at least two electrodes are in electrical contact with the electrolyte;
a means for exposing a surface of one or more of the at least two electrodes to one or more gases,
a means for producing an electric field proximate the surface, wherein the electric field modifies a catalysis reaction between the one or more gases and the one or more of the at least two electrodes.

Embodiment 43

The catalysis device according to Embodiment 42, wherein the electric field enhances the catalysis reaction between the one or more gases and the one or more of the at least two electrodes.

Embodiment 44

The catalysis device according to Embodiment 42, further comprising a means for exposing the electrolyte to the one or more gases, wherein the electric field modifies a catalysis reaction between the one or more gases and the electrolyte.

Embodiment 45

The catalysis device according to Embodiment 43, further comprising a means for exposing the electrolyte to the one or more gases, wherein the electric field modifies a catalysis reaction between the one or more gases and the electrolyte.

Embodiment 46

The catalysis device according to Embodiment 43, further comprising:
a means for applying a bias across two of the at least two electrodes.

Embodiment 47

The catalysis device according to Embodiment 46, wherein the means for applying the bias is a voltage source.

Embodiment 48

The catalysis device according to Embodiment 46, wherein the means for applying the bias is a current source.

Embodiment 49

The catalysis device according to Embodiment 42, wherein the substrate comprises a porous structure that allows the one or more gases to flow through, wherein the at least two electrodes comprise a plurality of particles within the porous structure.

Embodiment 50

A device, comprising:
a substrate, wherein the substrate comprises an electrolyte;
at least two electrodes positioned on the substrate, wherein the at least two electrodes are in electrical contact with the electrolyte; and
a means for creating an electric field proximate one or more of the at least two electrodes, wherein an output EMF is produced between the at least two electrodes when the one or more of at least two electrodes are exposed to one or more gases, wherein the electric field proximate the one or more of the at least two electrodes modifies the output EMF.

Embodiment 51

The device according to Embodiment 50, further comprising:
a load connected to the two of the at least two electrode, wherein power is delivered to the load.

Embodiment 52

The device according to Embodiment 50, wherein the two of the at least two electrodes are on opposite sides of the substrate, wherein a first gas is in contact with a first of the two electrodes, wherein the first gas reacts such that an ion of a component of the first gas and/or an ion of the first gas travels through the electrolyte to a second of the two electrodes and becomes the component of the first gas and/or the first gas, respectively.

Embodiment 53

The device according to Embodiment 52, further comprising:
a means for applying a bias across the two of the at least two electrodes.

Embodiment 54

The device according to Embodiment 53, wherein the means for applying the bias is a voltage source.

Embodiment 55

The device according to Embodiment 53, wherein the means for applying the bias is a current source.

Embodiment 56

A method, comprising:
providing a substrate, wherein the substrate comprises an electrolyte;
providing at least two sensing electrodes, wherein the at least two sensing electrodes are positioned on the substrate, wherein the at least two sensing electrodes are in contact with the electrolyte;
creating an electric field proximate at least one of the at least two sensing electrodes;
measuring a characteristic with respect to one or more of the at least two sensing electrodes, wherein creating the electric field proximate the at least two sensing electrodes alters the measured characteristic.

Embodiment 57

The method according to Embodiment 56, wherein the characteristic is an electrical characteristic.

Embodiment 58

The method according to Embodiment 56, wherein the characteristic is temperature.

Embodiment 59

The method according to Embodiment 57, wherein the electrical characteristic is a voltage between two of the at least two sensing electrodes.

Embodiment 60

The method according to Embodiment 57, wherein the electrical characteristic is a current flowing between two of the at least two sensing electrodes.

Embodiment 61

The method according to Embodiment 57, wherein the electrical characteristic is an impedance between two of the at least two sensing electrodes.

Embodiment 62

The method according to Embodiment 57, wherein the electrical characteristic is a resistance between two of the at least two sensing electrodes.

Embodiment 63

The method according to Embodiment 57, wherein the electrical characteristic is a capacitance between two of the at least two sensing electrodes.

Embodiment 64

The method according to Embodiment 56, further comprising:
modifying a temperature of at least one of the at least two sensing electrodes, wherein modifying the temperature alters the measured electrical characteristic.

Embodiment 65

The method according to Embodiment 64, further comprising:
monitoring the temperature of the at least one of the at least two sensing electrodes.

Embodiment 66

The method according to Embodiment 56, wherein the method is a method for sensing gas.

Embodiment 67

The method according to Embodiment 56, wherein creating the electric field is accomplished via a means for creating the electric field that is positioned on the substrate.

Embodiment 68

The method according to Embodiment 67, wherein the means for creating the electric field comprises at least one electric field electrode positioned on the substrate.

Embodiment 69

The method according to Embodiment 68, wherein the at least one sensing electrode and the at least one electric field electrode are positioned on opposite sides of the substrate.

Embodiment 70

The method according to Embodiment 67, wherein the at least one sensing electrode and the at least one electric field electrode are positioned on the same side of the substrate.

Embodiment 71

The method according to Embodiment 68, wherein each of the at least one electric field electrodes comprises a conducting layer and an insulation layer, wherein the insulation layer is positioned between the substrate and the conducting layer.

Embodiment 72

The method according to Embodiment 57, wherein the means for measuring the electrical characteristic with respect to one or more of the at least two sensing electrodes measures a time dependence of the electrical characteristic of the one or more of the at least two sensing electrodes.

Embodiment 73

The method according to Embodiment 66, wherein the gas sensor measures a concentration of a component of a gas mixture.

Embodiment 74

The method according to Embodiment 66, wherein the gas sensor detects a presence of a gas.

Embodiment 75

The method according to Embodiment 73, wherein a first of the at least two sensing electrodes is positioned on a first surface of the electrolyte, wherein a second of the at least two sensing electrodes is positioned on the first surface of the electrolyte, wherein the means for measuring a characteristic with respect to one or more of the at least two sensing electrodes comprises a means for measuring a voltage between the first sensing electrode and the second sensing electrode.

Embodiment 76

The method according to Embodiment 75, wherein the means for creating an electric field proximate at least one of the at least two sensing electrodes creates the electric field proximate the first sensing electrode.

Embodiment 77

The method according to Embodiment 76, wherein the means for creating the electric field creates the electric field proximate the second sensing electrode.

Embodiment 78

The method according to Embodiment 76, wherein the means for creating the electric field comprises at least one electric field electrode.

Embodiment 79

The method according to Embodiment 78, wherein the at least one electric field electrode comprises a first ring-shaped electrode surrounding the first sensing electrode.

Embodiment 80

The method according to Embodiment 56, further comprising a reference electrode positioned on the substrate.

Embodiment 81

The method according to Embodiment 73, wherein the component is NO.

Embodiment 82

The method according to Embodiment 73, wherein the component is $NO_2$.

Embodiment 83

The method according to Embodiment 73, wherein the component is selected from the following group: ammonia, $SO_2$, $SO_3$, hydrocarbons, $H_2$, $H_2O$, CO, and $CO_2$.

Embodiment 84

The method according to Embodiment 73, further comprising a means for determining the concentration of the component from the measured electrical characteristic.

Embodiment 85

The method according to Embodiment 56, wherein the means for creating the electric field is not in electrical contact with the substrate.

Embodiment 86

A method, comprising:
providing a substrate;
providing at least one sensing electrode, wherein the at least one sensing electrode is positioned on the substrate;
creating an electric field proximate one of the at least one sensing electrode;
measuring a characteristic with respect to the one of the at least one sensing electrode.

Embodiment 87

The method according to Embodiment 86, wherein the characteristic is an electrical characteristic.

Embodiment 88

The method according to Embodiment 87, wherein the electrical characteristic is an impedance of the one of the at least one sensing electrodes

Embodiment 89

The method according to Embodiment 87, wherein the electrical characteristic is a resistance of the one of at least one sensing electrode.

Embodiment 90

The method according to Embodiment 87, wherein the electrical characteristic is a capacitance of the one of at least one sensing electrode.

Embodiment 91

The method according to Embodiment 87, wherein measuring an electrical characteristic comprises measuring a time dependence of the electrical characteristic of the one of the at least one sensing electrodes.

Embodiment 92

The method according to Embodiment 87, wherein the substrate comprises an electrolyte, wherein the one of the at least one sensing electrode is in electrical contact with the electrolyte.

Embodiment 93

The method according to Embodiment 87, wherein the electrical characteristic is an impedance between two of the at least one sensing electrode.

Embodiment 94

The method according to Embodiment 86, wherein the characteristic is temperature.

Embodiment 95

The method according to Embodiment 94, further comprising:
modifying a temperature of at least one of the at least one sensing electrode, wherein modifying the temperature alters the measured electrical characteristic.

Embodiment 96

The method according to Embodiment 95, further comprising:
monitoring the temperature of the at least one of the at least one sensing electrode.

Embodiment 97

A method of modifying a catalysis reaction, comprising:
providing a substrate, wherein the substrate comprises an electrolyte;
providing at least two electrodes, wherein the at least two electrodes are in contact with the electrolyte;
exposing a surface of one or more of the at least two electrodes is exposed to one or more gases,
producing an electric field proximate the surface, wherein the electric field modifies a catalysis reaction between the one or more gases and the one or more of the at least two electrodes.

Embodiment 98

The method according to Embodiment 97, wherein the electric field enhances the catalysis reaction between the one or more gases and the one or more of the at least two electrodes.

Embodiment 99

The method according to Embodiment 98, further comprising exposing the electrolyte to the one or more gases, wherein the electric field modifies a catalysis reaction between the one or more gases and the electrolyte.

Embodiment 100

The method according to Embodiment 97, further comprising exposing the electrolyte to the one or more gases, wherein the electric field modifies a catalysis reaction between the one or more gases and the electrolyte.

Embodiment 101

The method according to Embodiment 98, further comprising:
applying a bias across two of the at least two electrodes.

Embodiment 102

The method according to Embodiment 101, wherein applying the bias comprises applying a voltage across the two of the at least two electrodes.

Embodiment 103

The method according to Embodiment 101, wherein applying the bias comprises applying a current across the two of the at least two electrodes.

Embodiment 104

The method according to Embodiment 97, wherein the substrate comprises a porous structure that allows the one or more gases to flow through, wherein the at least two electrodes comprise a plurality of particles within the porous structure.

Embodiment 105

A method, comprising:
providing a substrate, wherein the substrate comprises an electrolyte;
providing at least two electrodes positioned on the substrate, wherein the at least two electrodes are in electrical contact with the electrolyte; and
creating an electric field proximate one or more of the at least two electrodes, wherein an output EMF is produced between two of the at least two electrodes when the one or more of the at least two electrodes are exposed to one or more gases that react with the one or more of the at least two electrodes, wherein the electric field proximate the one or more of the at least two electrodes modifies the output EMF.

Embodiment 106

The method according to Embodiment 105, further comprising:
connecting a load to the two of the at least two electrode, wherein power is delivered to the load.

Embodiment 107

The method according to Embodiment 105, wherein the two of the at least two electrodes are on opposite sides of the substrate, wherein a first gas is in contact with a first of the two electrodes, wherein the first gas reacts such that an ion of a component of the first gas and/or an ion of the first gas travels through the electrolyte to a second of the two electrodes and becomes the component of the first gas and/or the first gas, respectively.

Embodiment 108

The method according to Embodiment 107, further comprising:
applying a bias across the two of the at least two electrodes.

Embodiment 109

The method according to Embodiment 108, wherein applying the bias is accomplished via a voltage source.

Embodiment 110

The device according to Embodiment 108, wherein applying the bias is accomplished via a current source.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A fuel cell, comprising:
an electrolyte;
a first electrode, wherein the first electrode is in electrical contact with the electrolyte;
a second electrode, wherein the second electrode is in electrical contact with the electrolyte; and
an electric field source,
wherein the electric field source is insulated from the electrolyte,
wherein the electric field source comprises a first electric-field electrode corresponding to the first electrode and a second electric-field electrode corresponding to the second electrode,
wherein the first electric-field electrode and the second electric-field electrode are physically separated from each other,
wherein the first electrode and the second electrode are disposed on the same surface of the electrolyte,
wherein the electric field source creates an electric field profile proximate one or both of the first electrode and the second electrode,
wherein creation of the electric field profile proximate the one or both of the first electrode and the second electrode via the electric field source does not result in the passage of current through the fuel cell,
wherein an output EMF is produced between the first electrode and the second electrode when the one or both of the first electrode and second electrode are exposed to one or more gases, and
wherein the fuel cell is configured such that, when the one or both of the first electrode and second electrode are exposed to the one or more gases, the electric field profile proximate the one or both of the first electrode and the second electrode modifies the output EMF.

2. The fuel cell according to claim 1, further comprising:
a load connected to the first electrode and the second electrode,
wherein power is delivered to the load.

3. The fuel cell according to claim 1, further comprising:
a substrate,
wherein the substrate comprises the electrolyte, and
wherein the first electrode and the second electrode are positioned on the substrate.

4. The fuel cell according to claim 3,
wherein the first electrode and the second electrode are on opposite sides of the substrate, wherein a first gas is in contact with the first electrode, and
wherein the first gas reacts such that an ion of a component of the first gas and/or an ion of the first gas travels through the electrolyte to the second electrode and becomes a component of a second gas and/or the second gas, respectively.

5. The fuel cell according to claim 3,
wherein the electric field source comprises:
at least two electric field electrodes; and
an electric field voltage source.

6. The fuel cell according to claim 5,
wherein the at least two electric field electrodes are positioned on the substrate and each electric field electrode of the at least two electric field electrodes is separated from the electrolyte by a corresponding insulator of at least two insulators positioned between the corresponding electric field electrode and the substrate.

7. The fuel cell according to claim 3, further comprising:
a second substrate,
wherein the second substrate comprises a second electrolyte;
two additional electrodes positioned on the second substrate,
wherein the two additional electrodes are in electrical contact with the second electrolyte; and
a second electric field source,
wherein the second electric field source creates a second electric field proximate one or both additional electrodes of the two additional electrodes,
wherein the second electric field source comprises at least two second electric field electrodes,
wherein the at least two second electric field electrodes are not in electrical contact with the second electrolyte,
wherein a second output EMF is produced between the two additional electrodes when the one or both additional electrodes of the two additional electrodes are exposed to a second one or more gases, and
wherein the second electric field proximate the one or both additional electrodes of the two additional electrodes modifies the second output EMF.

8. The fuel cell according to claim 7,
wherein the fuel cell has a stacked configuration.

9. A catalysis device, comprising:
a substrate, wherein the substrate comprises an electrolyte;
at least two electrodes, wherein the at least two electrodes are in electrical contact with the electrolyte; and
an electric field source,
wherein the electric field source is insulated from the electrolyte,
wherein the electric field source comprises at least two electric-field electrodes,
wherein each of the at least two electric-field electrodes corresponds to each of the at least two electrodes, respectively,
wherein the at least two electric-field electrodes are physically separated from each other,
wherein the electric field source creates an electric field profile proximate a corresponding one or more surfaces of one or more electrodes of the at least two electrodes, and
wherein, when the one or more surfaces of the one or more electrodes of the at least two electrodes are exposed to at least one gas, the electric field profile modifies a catalysis reaction between the at least one gas and the one or more surfaces of the one or more electrodes of the at least two electrodes.

10. The catalysis device according to claim 9,
wherein, when the one or more surfaces of the one or more electrodes of the at least two electrodes are exposed to the at least one gas, the electric field profile enhances the catalysis reaction between the at least one gas and the one or more surfaces of the one or more electrodes of the at least two electrodes.

11. The catalysis device according to claim 9, further comprising:
a voltage source,
wherein the voltage source is configured to apply a bias across two electrodes of the at least two electrodes.

12. The catalysis device according to claim 9, further comprising:
a current source,
wherein the current source is configured to apply a bias across two electrodes of the at least two electrodes.

13. The catalysis device according to claim 9,
wherein the substrate comprises a porous structure that allows the at least one gas to flow through at least a portion of the porous structure, and
wherein the at least two electrodes comprise a plurality of particles within the porous structure.

14. The catalysis device according to claim 9,
wherein, when the electrolyte is exposed to the at least one gas, the electric field profile modifies a catalysis reaction between the at least one gas and the electrolyte.

15. The catalysis device according to claim 14,
wherein, when the electrolyte is exposed to the at least one gas, the electric field profile enhances the catalysis reaction between the at least one gas and the electrolyte.

16. An electrochemical cell, comprising:
a substrate, wherein the substrate comprises an ionically conducting electrolyte;
at least two sensing electrodes, wherein the at least two sensing electrodes are positioned on the substrate, wherein the at least two sensing electrodes are in electrical contact with the ionically conducting electrolyte; and
an electric field source,
wherein the electric field source comprises at least two electric field electrodes and at least one voltage source,
wherein the at least two electric field electrodes are not in electrical contact with the ionically conducting electrolyte,
wherein each of the at least two electric field electrodes corresponds to each of the at least two sensing electrodes, respectively,
wherein the at least two electric field electrodes are physically separated from each other,
wherein the at least two sensing electrodes are disposed on the same surface of the substrate,
wherein the at least one voltage source is configured to apply a first voltage biasing scheme to the at least two electric field electrodes during a first period of time, so as to create an electric field profile proximate at least one sensing electrode of the at least two sensing electrodes during the first period of time such that the electric field profile proximate the at least one sensing electrode comprises a non-zero electric field proximate the at least one sensing electrode at a first point in time during the first period of time,
wherein the application of the first voltage biasing scheme to the at least two electric field electrodes during the first period of time does not cause the passage of current through the substrate during the first period of time; and
a measurement device,
wherein the measurement device is configured to measure a value of a characteristic with respect to one or more of the at least two sensing electrodes during at least a portion of the first period of time incorporating the first point in time,
wherein the one or more of the at least two sensing electrodes comprises the at least one sensing electrode,
wherein the value of the characteristic with respect to the one or more of the at least two sensing electrodes is:
a corresponding one or more temperatures of the one or more of the at least two sensing electrodes, or
an electrical characteristic with respect to the one or more of the at least two sensing electrodes,
wherein the electrical characteristic with respect to the one or more of the at least two sensing electrodes is selected from the group consisting of:
a voltage between two of the at least two sensing electrodes,
a current flowing between two of the at least two sensing electrodes,
an impedance between two of the at least two sensing electrodes,
a resistance between two of the at least two sensing electrodes, and
a capacitance between two of the at least two sensing electrodes, and
wherein the electrochemical cell is configured such that when the at least one sensing electrode is exposed to a target gas component in a gas at the first point in time, the electric field profile proximate the at least one of the at least two sensing electrodes causes the value of the measured characteristic with respect to the one or more of the at least two sensing electrodes to be different than the value of the measured characteristic with respect to the one or more of the at least two sensing electrodes if the first voltage biasing scheme was not applied to the at least two electric field electrodes during the first period of time.

17. The electrochemical cell according to claim 16,
wherein the at least two electric field electrodes are separated from the ionically conducting electrolyte by one or more insulators.

* * * * *